(12) United States Patent
Fukunishi et al.

(10) Patent No.: US 6,174,885 B1
(45) Date of Patent: Jan. 16, 2001

(54) [6-(SUBSTITUTED-METHYL)-3-CYCLOHEXENYL] FORMAMIDE DERIVATIVE, HAIR GROWTH PROMOTER AND EXTERNAL COMPOSITION FOR SKIN

(75) Inventors: Hirotada Fukunishi; Tsunao Magara; Koji Kobayashi, all of Kanagawa (JP)

(73) Assignee: Shiseido Co., Ltd., Tokyo (JP)

( * ) Notice: Under 35 U.S.C. 154(b), the term of this patent shall be extended for 0 days.

(21) Appl. No.: 09/257,940

(22) Filed: Feb. 26, 1999

(30) Foreign Application Priority Data

Mar. 3, 1998 (JP) .................................................. 10-069581

(51) Int. Cl.$^7$ ...................... A61K 31/535; A61K 31/495; A61K 31/445; C07D 295/18; C07D 211/32
(52) U.S. Cl. .................. 514/237.8; 514/255.01; 514/331; 514/489; 514/551; 514/552; 514/613; 544/169; 544/389; 546/233; 554/106; 560/32; 560/162; 564/123; 564/191
(58) Field of Search ............................ 514/237.8, 255.01, 514/331, 489, 551, 552, 613; 544/169, 389; 546/233; 554/106; 560/32, 162; 564/123, 191

(56) References Cited

U.S. PATENT DOCUMENTS 4,628,061 * 12/1986 Jones et al. ........................... 514/469

FOREIGN PATENT DOCUMENTS

| 0 811 370 A1 | 12/1997 | (EP) . |
| 7-304736 | 11/1995 | (JP) . |
| 7-316022 | 12/1995 | (JP) . |
| 7-316023 | 12/1995 | (JP) . |
| 8-020521 | 1/1996 | (JP) . |
| 8-026942 | 1/1996 | (JP) . |

\* cited by examiner

*Primary Examiner*—Mukund J. Shah
*Assistant Examiner*—Brenda Coleman
(74) *Attorney, Agent, or Firm*—Ronald R Snider; Snider & Associates

(57) ABSTRACT

A [6-(substituted-methyl)-3-cyclohexenyl]formamide derivative or a salt thereof expressed by the following Formula (I):

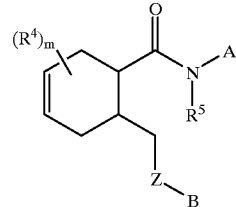

(I)

wherein one of A and B is a hydrocarbon group of $C_{10-30}$ expressed by $R^1$ and the other is —$(CH_2)n$-$NR^2R^3$; Z is —O—, —OCO—, —OCONR$^6$— or —NR$^6$—; $R^2$ and $R^3$ individually represent a hydrogen, lower alkyl, phenyl or benzyl group, or together represent a heterocycle having 3–7 members; —NR$^5$—$(CH_2)n$-$NR^2R^3$ or —NR$^6$—$(CH_2)n$-$NR^2R^3$ may be Group W, and —OCONR$^6$—$(CH_2)n$-$NR^2R^3$ may be —OCO—W, wherein W is a formula of:

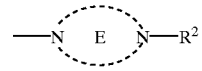

(W)

wherein ring E is a heterocycle of 6 or 7 members including two nitrogen atoms and $R^2$ is a hydrogen, lower alkyl, phenyl or benzyl group; $R^4$ is a halogen, lower alkyl, lower acyl, nitro, cyano, lower alkoxycarbonyl, carbamoyl, lower alkylcarbamoyl, lower alkylamino, lower acylamino, lower alkoxy or lower acyloxy group; each of $R^5$ and $R^6$ is a hydrogen, lower alkyl, lower acyl, lower alkylcarbamoyl group, or a part of said Group W; m is an integer of 0–2; and n is an integer of 0–5. The [6-(substituted-methyl)-3-cyclohexenyl]formamide derivative or the salt thereof has excellent hair growth and regrowth promoting effects, which are useful for care, improvement or prevention of hair loss in mammals and, in particular, in human.

17 Claims, 13 Drawing Sheets

Reaction Formula AA

Reaction Formula AB

Reaction Formula AC

Reaction Formula AD

Reaction Formula AE

Reaction Formula AF

Reaction Formula BA

Reaction Formula BB

Reaction Formula CA

Reaction Formula CB

Reaction Formula CC

Reaction Formula DA

Reaction Formula DB

Reaction Formula EA

Reaction Formula EB

Reaction Formula EC

Reaction Formula FA

Reaction Formula FB

Reaction Formula GA

Reaction Formula GB

Reaction Formula GC

Reaction Formula HA

Reaction Formula HB

Reaction Formula HC

Reaction Formula IA

US 6,174,885 B1

[6-(SUBSTITUTED-METHYL)-3-CYCLOHEXENYL] FORMAMIDE DERIVATIVE, HAIR GROWTH PROMOTER AND EXTERNAL COMPOSITION FOR SKIN

FIELD OF THE INVENTION

The present invention relates to a [6-(substituted-methyl)-3-cyclohexenyl]formamide derivative and, in particular, to a [6-(substituted-methyl)-3-cyclohexenyl]formamide derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, generation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin $B_6$.

In addition to these drugs, salicylic acid, resorcine and the like that have comeocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acids, vitamins, extracts of crude drugs and the like can be compounded so as to aliment to hair follicle and activate enzyme activity.

Meanwhile, for example, D (L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain [6-(substituted-methyl)-3-cyclohexenyl]formamide derivative and its salt have excellent hair growth and regrowth promoting effect, thereby accomplishing the present invention.

Namely, a [6-(substituted-methyl)-3-cyclohexenyl] formamide derivative or a salt thereof in accordance with the present invention is expressed by the following Formula (I):

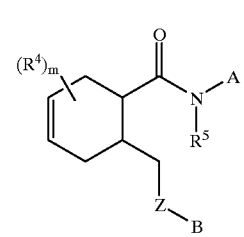

(I)

wherein
each of A and B is $R^1$ or —$(CH_2)n$-$NR^2R^3$, wherein when A is $R^1$, B is —$(CH_2)n$-$NR^2R^3$ and when A is —$(CH_2)n$-$NR^2R^3$, B is $R^1$;

Z is —O—, —OCO—, —OCONR$^6$— or —NR$^6$—;

$R^1$ is a hydrocarbon group of $C_{10-30}$;

$R^2$ and $R^3$ individually represent a hydrogen atom, a lower alkyl group, a phenyl group or a benzyl group, or together represent a heterocycle having 3–7 members;

when A is —$(CH_2)n$-$NR^2R^3$, —$NR^5$—A may be Group W, and when —Z—B is —OCONR$^6$—$(CH_2)n$-$NR^2R^3$ or —NR$^6$—$(CH_2)n$-$NR^2R^3$, —Z—B may be a group of —OCO—W or Group W, wherein said Group W is expressed by the following Formula:

(W)

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group, and when A is —$(CH_2)n$-$NR^2R^3$, —$NR^5$—A may be said Group W;

$R^6$ is a hydrogen atom, a lower alkyl group, a lower acyl group or a lower alkylcarbamoyl group, and when —Z—B is —OCONR$^6$—$(CH_2)n$-$NR^2R^3$ or —NR$^6$—$(CH_2)n$-$NR^2R^3$, —Z—B may be —OCO—W or said Group W;

m is an integer of 0–2; and n is an integer of 0–5.

A hair growth promoting composition in accordance with the present invention is characterized by comprising said

[6-(substituted-methyl)-3-cyclohexenyl]formamide derivative or the pharmacologically acceptable salt thereof as an effective ingredient.

An external preparation for skin in accordance with the present invention is characterized by comprising said [6-(substituted-methyl)-3-cyclohexenyl]formamide derivative or the pharmacologically acceptable salt thereof.

A method for promoting hair growth in accordance with the present invention is characterized by applying an effective amount of said [6-(substituted-methyl)-3-cyclohexenyl] formamide derivative or the pharmacologically acceptable salt thereof on the skin of mammals and, in particular, on human scalp.

BEST MODE FOR CARRYING OUT THE INVENTION

Figure 1:
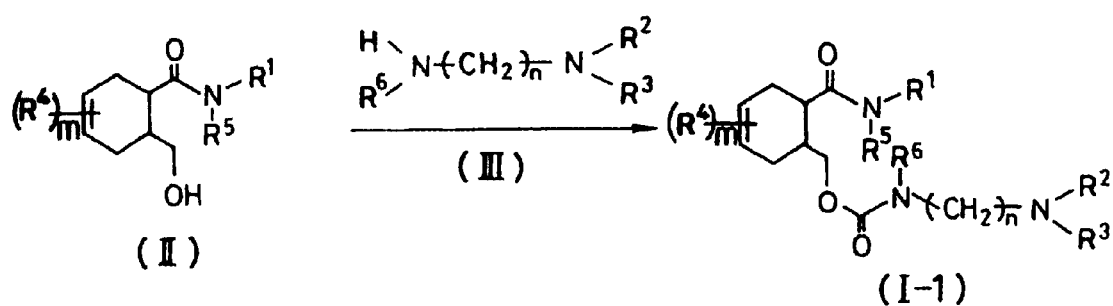
FIGS. 1–4 and 7–23 show examples of steps for manufacturing the [6-(substituted-methyl)-3-cyclohexenyl] formamide derivative in accordance with the present invention.

In a compound of the present invention, a hydrocarbon group of $C_{10-30}$ shown by $R^1$ refers to a straight or branched alkyl group having 10–30 carbon atoms, a straight or branched alkenyl group having 10–30 carbon atoms or a straight or branched alkynyl group having 10–30 carbon atoms and may have a saturated ring or aromatic ring in $R^1$.

Examples of the above-mentioned straight alkyl group include decyl, undecyl, dodecyl, tridecyl, tetradecyl, pentadecyl, hexadecyl, heptadecyl, octadecyl, nonadecyl, icosyl, henicosyl, docosyl, tetracosyl, hexacosyl octacosyl and the like.

Examples of the above-mentioned branched alkyl group include 6-methyldecyl, 9-methyldecyl, 6-ethylnonyl, 5-propyloctyl, 11-methyldodecyl, 12-methyltridecyl, 4-methyltetradecyl, 13-methyltetradecyl, 14-ethylhexadecyl, 10-methyloctadecyl, 15-ethylheptadecyl, 10-methyldocosyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of the straight or branched alkenyl group having 10–30 carbon atoms and straight or branched alkynyl group having 10–30 carbon atoms include the alkenyl or alkynyl groups corresponding to the above-mentioned alkyl groups such as 4-decenyl, 7-dodecenyl, 9-octadecenyl or 3-dodecynyl.

Also, examples of the hydrocarbon group having a saturated ring or an aromatic ring in $R^1$ include 12-cyclohexyldodecyl, 4-butylphenyl, 8-phenyloctyl, biphenylyl and the like.

Among these groups, $R^1$ is preferably a straight or branched alkyl group having 10–30 carbon atoms and, more preferably, a straight or branched alkyl group having 10–20 carbon atoms and, particularly preferably, octadecyl group. Also, when —Z—B is —OCO—$R^1$, $R^1$ is preferably heptadecyl group. The hair growth effect tends to deteriorate in the case where the carbon number of $R^1$ is too small.

Each of $R^2$ and $R^3$, which may be identical or different from each other, can be a hydrogen, a lower alkyl, a phenyl or a benzyl group. Also, $R^2$ and $R^3$ together can represent a heterocycle having 3–7 members. Further, when A is —(CH$_2$)n-NR$^2$R$^3$, —NR$^5$—A may be said Group W. Furthermore, when —Z—B is —OCONR$^6$—(CH$_2$)n-NR$^2$R$^3$ or —NR$^6$—(CH$_2$)n-NR$^2$R$^3$, —Z—B may be a group of —OCO—W or said Group W.

In $R^2$ and $R^3$, the lower alkyl group refers to a straight or branched alkyl group having 1–6 carbon atoms. Examples of the lower alkyl group include methyl, ethyl, propyl, butyl, isopropyl, isobutyl, 1-methylpropyl, tert-butyl, pentyl, 1-ethylpropyl, isoamyl, hexyl and the like. For the lower alkyl group in $R^2$ and $R^3$, methyl or ethyl group is preferable. In the present invention, the definition of lower alkyl group is the same as mentioned above if there is no further description.

Also, the lower alkyl group in $R^2$ and $R^3$ may be substituted by a hydroxyl group. Examples of such a hydroxy lower alkyl group include 2-hydroxyethyl group. In $R^2$ and $R^3$, a phenyl and a benzyl group may be unsubstituted or substituted by a halogen, a lower alkyl, a lower acyl, a nitro, a cyano, a lower alkoxycarbonyl, a lower alkylamino, a lower alkoxy or a lower acyloxy group, respectively. The definition of each substituent referred in here is explained as follows.

The halogen atom represents chlorine, bromine, iodine or fluorine.

The lower alkyl group is as mentioned above and, preferably, methyl or ethyl group.

The lower acyl group is a straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two of the same or different lower alkyl group. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

In $R^2$ and $R^3$, the heterocycle having 3–7 members which is formed by $R^2$ and $R^3$ together represents a saturated or unsaturated heterocycle having 3–7 members containing nitrogen atom to which $R^2$ and $R^3$ are bonded. In addition to the nitrogen atom, a hetero atom such as nitrogen atom or oxygen atom may be contained in the heterocycle. Examples of the heterocycle include aziridine, azetidine, pyrrolidine, piperidine, homopiperidine, piperazine, morpholine, pyrrole, pyrazole, and imidazole ring. Among these heterocycles, pyrrolidine, piperidine, piperazine or morpholine ring is preferable. The heterocycle may be substituted by one or two of the same or different substituent. Such a substituent can be selected from the group consisting of a lower alkyl, a lower alkoxy, a lower acyl and a nitro group. The lower alkyl group is preferably methyl or ethyl group. The lower alkoxy group is preferably methoxy or ethoxy group. The lower acyl group is preferably acetyl or propionyl, or butyryl group.

In said Group W, the heterocyclic ring E having 6–7 members can be formed by $R^3$ together with $R^5$ or $R^6$ to contain two nitrogen atoms. $R^2$ in Group W can be a hydrogen, a lower alkyl, a phenyl or a benzyl group and, preferably, methyl or benzyl group. As for the heterocyclic ring E, a piperazine ring is preferable.

In the present invention, it is preferable that $R^2$ and $R^3$ are lower alkyl groups, or together forms a heterocycle having 3–7 members or a part of Group W.

$R^4$ can be a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group or a lower acyloxy group.

As for $R^4$, the definitions for halogen, lower alkyl, lower acyl, lower alkoxycarbonyl, lower alkylamino, lower alkoxy and lower acyloxy groups are identical to those in $R^2$ and $R^3$.

The lower alkylcarbamoyl group in $R^4$ represents a carbamoyl group whose one or two hydrogen atoms are substituted by a lower alkyl group. A preferable example of the lower alkylcarbamoyl group is methylcarbamoyl or ethylcarbamoyl group.

The lower acylamino group in $R^4$ represents an amino group whose one or two hydrogen atoms are substituted by a lower acyl group. The lower acyl group is as mentioned above. A preferable example of the lower acylamino group is acetylamino, propionylamino or benzoylamino group.

Among them, $R^4$ is preferably a lower alkyl group and, more preferably, methyl group.

$R^5$ can be a hydrogen atom, a lower alkyl group, a lower acyl group or a lower alkylcarbamoyl group. Also, when A is —(CH$_2$)n-NR$^2$R$^3$, —NR$^5$—A may be said Group W. Preferably, $R^5$ is a hydrogen atom.

$R^6$ can be a hydrogen atom, a lower alkyl group, a lower acyl group or a lower alkylcarbamoyl group. Also, when —Z—B is —OCONR$^6$—(CH$_2$)n-NR$^2$R$^3$ or —NR$^6$—(CH$_2$)n-NR$^2$R$^3$, —Z—B may be —OCO—W or Group W. Preferably, $R^6$ is a hydrogen atom or forms a part of Group W.

As for $R^5$ and $R^6$, the definitions for lower alkyl and lower acyl groups are identical to those in $R^2$ and $R^3$ and the definition for lower alkylcarbamoyl group is identical to that in $R^4$.

Z is a divalent group expressed by —O—, —OCO—, —OCONR$^6$— or —NR$^6$— and, preferably, —OCONR$^6$—, —NR$^6$— or —O— and, particularly preferably, —OCONR$^6$—.

In the present invention, m is an integer of 0–2 and, preferably, 0.

Also, n is an integer of 0–5 and, preferably, an integer of 2–5.

In the present invention, a preferable example of a compound having Group W may be expressed by the following Formula (IA):

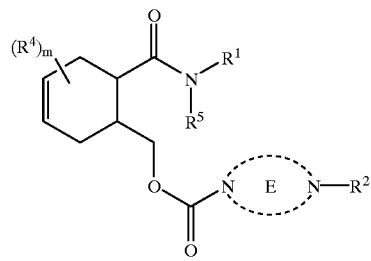

(IA)

wherein ring E is a heterocycle of 6 or 7 members including two nitrogen atoms;

$R^1$ is a hydrocarbon group of $C_{10-30}$;

$R^2$ is a hydrogen atom, a lower alkyl group, a phenyl group or a benzyl group;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group, or a lower alkylcarbamoyl group; and m is an integer of 0–2.

The Compound(I) of the present invention may have two or more asymmetric carbons in its molecule. In addition to optical isomers based on such asymmetric carbons, the present invention can include the other isomers such as geometrical isomers or conformational isomers, and also include the mixture thereof.

The Compound (I) provided in the present invention can be manufactured by using well-known reactions. Although the representative synthetic examples will be shown in the following, the present invention should not be restricted thereto. Also, in the following manufacturing methods, $R^1$, $R^2$, $R^3$, $R^4$, $R^5$, $R^6$, m and n are the same as shown in the definitions of Formula (I), unless otherwise indicated.

Compound (I-1) (A=$R^1$, B=—(CH$_2$)n-NR$^2$R$^3$, Z=—OCONR$^6$—)

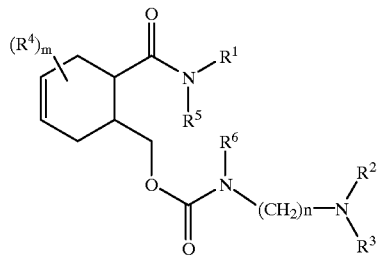

(I-1)

Compound (I-1) of the present invention can be synthesized by reacting Compound (II) with an amine (III) as shown in Reaction Formula AA of FIG. 1.

In this reaction, using phenyl chlorocarbonate, phosgene, diphosgene, triphosgene, di-2-pyridylketone or the like, Compound (II) is converted into its corresponding carbonate. Then, the carbonate is reacted with the amine (III). As an additive, for example, a base such as triethylamine, N,N-diisopropylethylamine, pyridine or sodium carbonate can be used. As a solvent, for example, a halogenated hydrocarbon such as dichloromethane or chloroform; an aromatic compound such as benzene, toluene, or xylene; or an ether such as tetrahydrofuran or 1,4-dioxane can be used. While the reaction temperature and reaction time may be changed according to the starting materials and the reagents used, the reaction is usually effected at a temperature within the range of −15° C. to 200° C. Specifically, for example, by using pyridine or N,N-diisopropylethylamine as an additive, Compound (II) is reacted with phenyl chlorocarbonate or triphosgene in a solvent such as chloroform or dichloromethane at a temperature within the range of −15° C. to room temperature to produce its corresponding carbonate. Then, the carbonate is reacted with the amine (III) in the absence or presence of a solvent such as chloroform or dichloromethane at a temperature of room temperature to 100° C., thereby attaining the aimed object.

In this reaction, a compound wherein $R^6$ is a hydrogen atom can be also synthesized by addition reaction of Compound (II) with the corresponding isocyanate, OCN—(CH$_2$)n-NR$^2$R$^3$. In this addition reaction, the isocyanate group is added to a hydroxyl group of Compound (II) to form a carbamoyloxy group, —OCONH—. As an additive, for example, an acid such as boron trifluoride, hydrochloric acid, aluminum chloride, dialkyltin dichloride or dialkyltin acetate, or a base such as triethylamine, N,N-diisopropylethylamine, pyridine, N-methylmorpholine, N-methylpiperidine, or sodium acetate can be used. As a solvent, for example, a halogenated hydrocarbon such as dichloromethane or chloroform; an aromatic compound such as benzene, toluene, or xylene; an ether such as tetrahydrofuran or 1,4-dioxane; or an amide such as N,N-dimethylformamide or N,N-dimethylacetamide can be used. While the reaction temperature and reaction time may be changed according to the starting materials and the reagents used, the reaction is usually effected at a temperature within the range of 0° C. to the reflux temperature of the solvent. Specifically, for example, by using triethylamine as an additive, Compound (III) is reacted with the isocyanate in a solvent such as dichloromethane at a temperature within the range of 0° C. to room temperature, thereby attaining the aimed object.

Such isocyanates can be commercially available or obtained by a reaction wherein the corresponding amine (III) is reacted with phosgene, diphosgene, triphosgene or the like in the absence or presence of a base, or by a reaction wherein a corresponding carboxylic acid HO$_2$C—(CH$_2$)n-NR$^2$R$^3$, is reacted with diphenylphosphoryl azide or the like in the presence of a base. As a base in this reaction, for example, an organic base such as triethylamine, N,N-diisopropylethylamine or pyridine can be used. As a solvent, for example, a halogenated hydrocarbon such as dichloromethane or chloroform; an aromatic compound such as benzene, toluene, or xylene; an ether such as tetrahydrofuran or 1,4-dioxane; or an amide such as N,N-dimethylformamide or N,N-dimethylacetamide can be used.

This carbamoyloxy group forming reaction by a hydroxyl group and an isocyanate can be used in Reaction Formulae AB to AC and EA to EC mentioned later. Also, the isocyanates used in each Reaction Formulae can be synthesized in the similar manner to the above.

Figure 2:
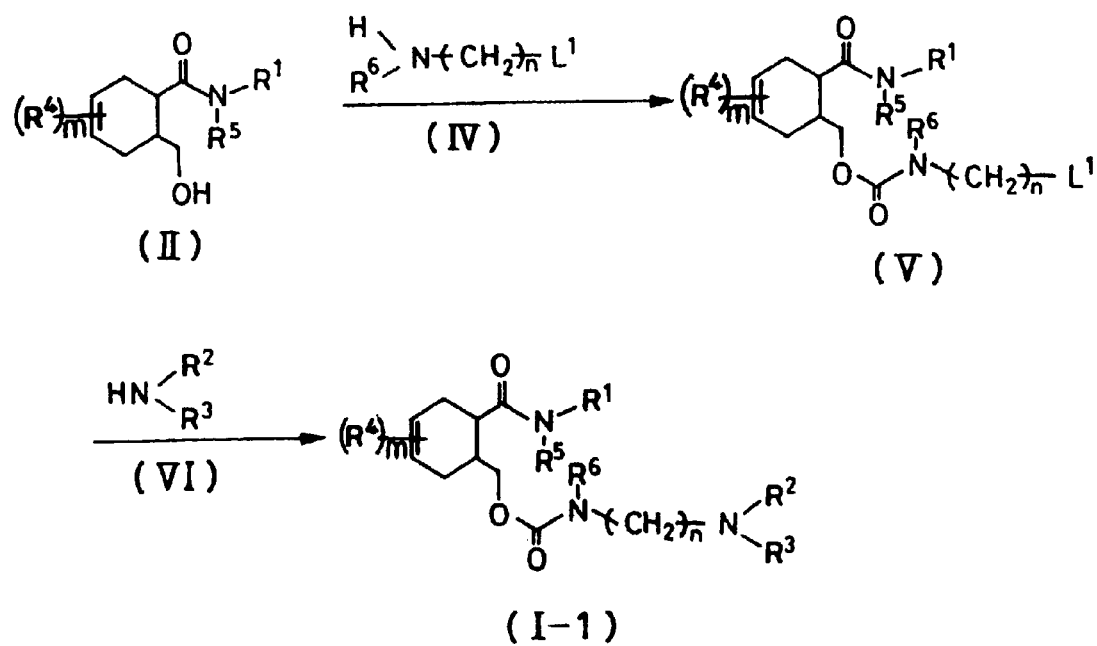

The Compound (I-1) can be also synthesized as shown in Reaction Formula AB of FIG. 2. First, Compound (V) is synthesized from Compound (II) and an amine (IV). Then, Compound (V) is reacted with an amine (VI), thereby producing Compound (I-1). Here, $L^1$ represents an atom or a group which is substituted by nitrogen easily and can be a halogen, tosyloxy, mesyloxy group or the like. The definition of $L^1$ throughout the rest of this specification is the same as stated above.

The first step of Reaction Formula AB can be effected according to Reaction Formula AA.

The reaction at the second step in Reaction Formula AB can be effected in the presence of a base. As a base, for example, an inorganic base such as potassium carbonate, potassium hydroxide, sodium hydroxide or sodium hydride, or an organic base such as triethylamine or pyridine can be used. As a solvent, toluene, ether, tetrahydrofuran, acetone, N,N-dimethylformamide or the like can be used. Specifically, for example, by using potassium carbonate as a base, the reaction is effected in a solvent such as acetone or N,N-dimethylformamide at the temperature with the range of room temperature to the reflux temperature of the solvent, thereby attaining the aimed object.

Figure 3:
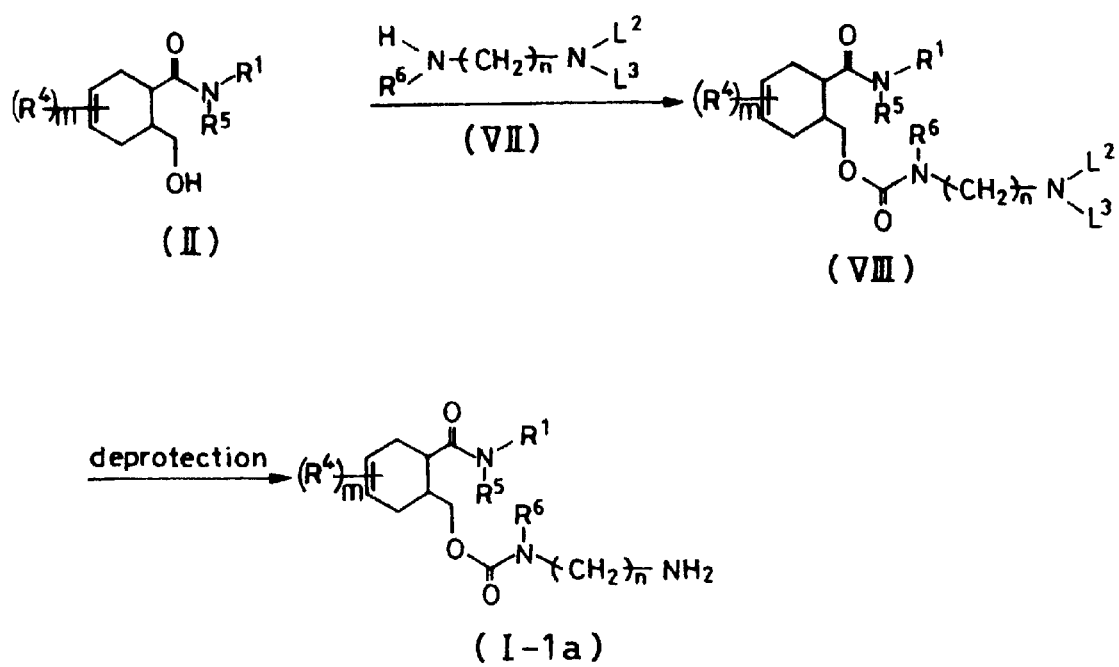

Also, Compound (I-1a) wherein $R^2$ and $R^3$ of Compound (I-1) are hydrogen atoms can be synthesized as shown in Reaction Formula AC of FIG. 3. First, Compound (II) is reacted with an amine (VII) to produce Compound (VIII). Then, Compound (VIII) is deprotected to produce Compound (I-1a). In Reaction Formula AC, either $L^2$ or $L^3$ can be an amino protecting group such as an urethane type protecting group (e.g., tert-butoxycarbonyl, benzyloxycarbonyl or 9-fluorenylmethyloxycarbonyl group), a sulfonyl type protecting group (e.g., 2-(trimethylsilyl)ethanesulfonyl group), a sulfenyl type protecting group (e.g., 2, 2, 2-trifluoro-1,1-diphenylethanesulfenyl group), or an alkyl type protecting group (e.g., benzyl, trityl or 9-phenylfluorenyl group), while the other can be a hydrogen atom. Also, $L^2$ and $L^3$ together can form a phthalimide type amino protecting group. Further, other protecting group can be used unless it is adverse to the object of this Reaction Formula. The definition of $L^2$ and $L^3$ throughout the rest of this specification is the same as stated above.

The first step in Reaction Formula AC can be effected according to Reaction Formula AA.

For the deprotection at the second step in Reaction Formula AC, various kind of known methods can be used according to the type of amino protecting group $L^2$ and $L^3$. Specifically, for example, in the case where $L^2$ and $L^3$ together form a phthalimide type amino protecting group, by using hydrazine as a deprotection agent, the reaction is effected in ethanol at a temperature within the range of room temperature to the reflux temperature of the solvent, thereby attaining the aimed object.

Figure 4:
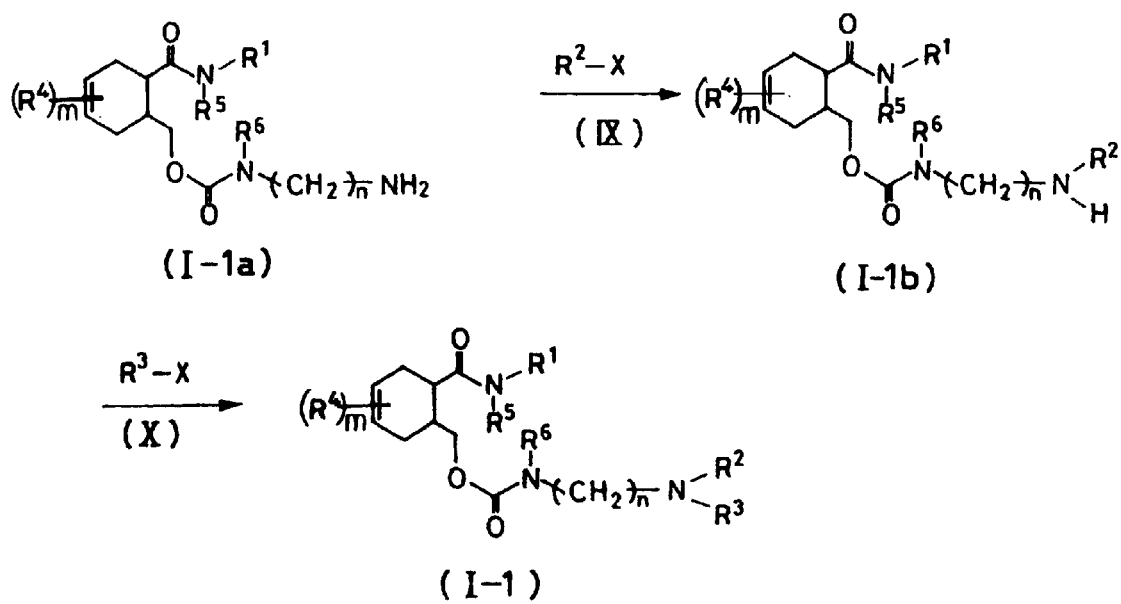

This Compound (I-1a), as shown in Reaction Formula AD of FIG. 4, can be converted into Compound (I-1b) by reacting with about one equivalent amount of a halide (IX) in the presence of a base. Further, Compound (I-1) can be obtained by reacting Compound (I-1b) with a halide (X) in the similar manner to the above. X represents a halogen atom. The definition of X throughout the rest of this specification remains the same.

In this reaction, when $R^2$ and $R^3$ are lower alkyl, phenyl or benzyl groups, an inorganic base such as potassium carbonate, potassium hydroxide, sodium hydroxide or sodium hydride; or an organic base such as triethylamine or pyridine can be used as a base. Specifically, for example, by using potassium carbonate as a base, the reaction is effected in a solvent such as acetone or N,N-dimethylformamide at a temperature within the range of room temperature to the reflux temperature of the solvent, thereby attaining the aimed object.

In the similar manner to this Reaction Formula AD, by reacting Compound (I-1a) with about twice equivalent amount of halide (IX) in the presence of a base, a compound wherein $R^2$ and $R^3$ of Compound (I-1) are the same can be obtained. Also, by reacting Compound (I-1a) with a suitable dihalogenated compound, a compound wherein $R^2$ and $R^3$ of Compound (I-1) together form a heterocycle having 3–7 members can be obtained.

Although a compound wherein $R^5$ or $R^6$ in Compound (I-1) is a lower alkyl, a lower acyl, or a lower alkylcarbamoyl group can be synthesized according to the above-mentioned Reaction Formulae, it can be also synthesized as follows. First, a compound wherein $R^5$ or $R^6$ of Compound (I-1) is a hydrogen atom is synthesized according to the above-mentioned Reaction Formulae. Then, the resulting compound is reacted with the corresponding halide such as alkyl halide, acyl halide, or alkylcarbamoyl halide in the absence or presence of a base. This is the same in the synthesis of Compounds (I-2) to (I-8) mentioned later.

Figure 5:
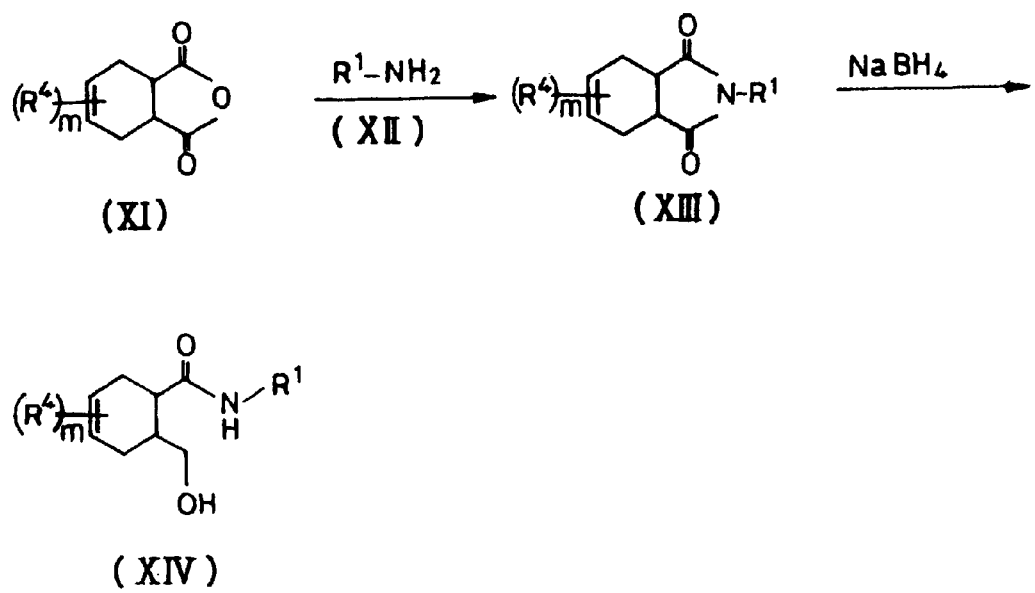
FIGS. 5, 6, and 25 show examples of steps for manufacturing starting materials of the [6-(substituted-methyl)-3-cyclohexenyl]formamide derivative in accordance with the present invention.
Figure 6:
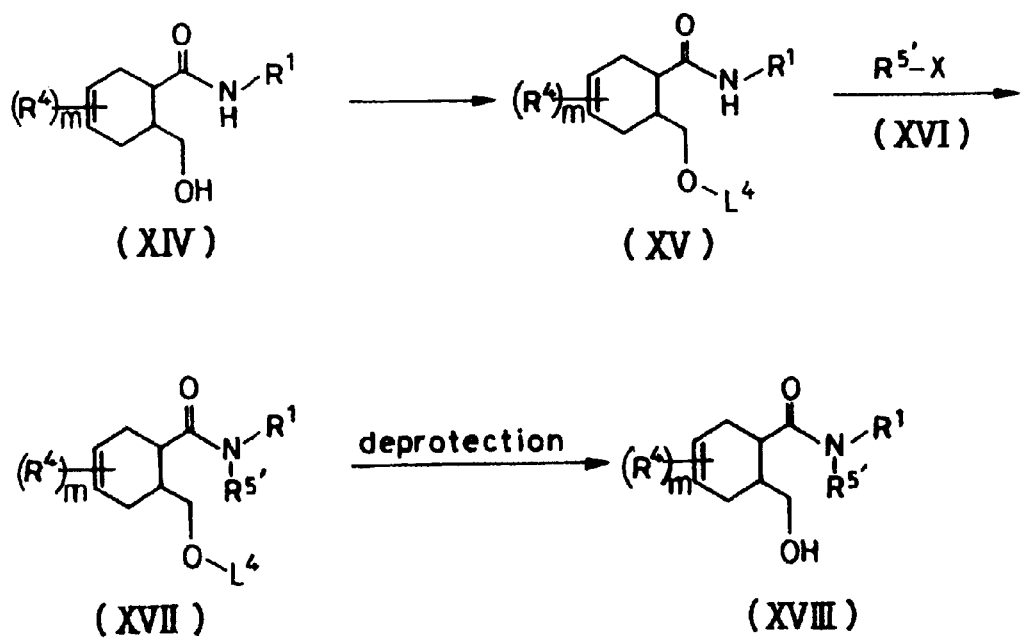

The starting materials in Reaction Formulae AA to AC can be synthesized by Reaction Formulae AE to AF of FIGS. 5 to 6.

In Reaction Formula AE, an imide (XIII) synthesized from an acid anhydride (XI) and an amine (XII) can be subjected to ring-opening reaction and reduction by using sodium borohydride, thereby producing Compound (XIV) wherein $R^5$ of Compound (II) is a hydrogen atom.

The reaction at the first step in Reaction Formula AE can be effected with or without a solvent. As a solvent, for example, a halogenated hydrocarbon such as dichloromethane or chloroform; an aromatic hydrocarbon such as benzene, toluene, xylene or pyridine; an ether such as tetrahydrofuran or 1,4-dioxane; an amide such as N,N-dimethylformamide or N,N-dimethylacetoamide; or a sulfoxide such as dimethylsulfoxide can be used. The reaction temperature can be within the range of room temperature to 150° C. Preferably, the reaction is effected without a solvent at a temperature of room temperature to 100° C.

The reaction by sodium borohydride at the second step, for example, can be effected in water or a mixed solvent of water with an alcohol such as ethanol or 2-propanol. While the reaction temperature and reaction time may be changed according to the starting materials and the reagents used, the reaction is usually effected at a temperature within the range of room temperature to the reflux temperature of the solvent.

Compound (XVIII) wherein $R^5$ of the starting Compound (II) is a lower alkyl, lower acyl, or lower alkylcarbamoyl group can be synthesized from Compound (XIV) obtained in Reaction Formula AE. For example, as shown in Reaction Formula AF, after a hydroxyl group of Compound (XIV) is protected, the resulting compound is reacted with a halide (XVI) to introduce $R^{5'}$ thereto and then deprotected, thereby producing Compound (XVIII). $R^{5'}$ is a lower alkyl, lower acyl, or lower alkylcarbamoyl group. The definition of $R^{5'}$ throughout the rest of this specification remains the same.

At the first step in Reaction Formula AF, as a hydroxyl-protecting group $L^4$, a protecting group stable in a basic condition can be used. For example, trityl, tetrahydropyranyl group(THP), or the like can be used. In the case of the protection using a trityl group, a halide such as trityl bromide is reacted with Compound (XIV) in the presence of a base. As a base, an inorganic base such as potassium carbonate, potassium hydroxide, sodium hydroxide or sodium hydride or an organic base such as triethylamine or pyridine can be used. Specifically, for example, by using potassium carbonate as a base, the reaction is effected in a solvent such as acetone or N,N-dimethylformamide at the temperature within a range of room temperature to the reflux temperature of the solvent, thereby producing Compound (XV). In the case of the protection using THP, 2,3-dihydro-4H-pyrane may be reacted with Compound (XIV) in an acidic condition.

The second step in Reaction Formula AF can be effected by reacting Compound (XV) with the corresponding halide (XVI) such as alkyl halide, acyl halide, or alkylcarbamoyl halide in the absence or presence of a base.

In the deprotecting reaction at the third step of Reaction Formula AF, various kinds of known methods can be used according to the kind of the protecting group $L^4$. For example, when $L^4$ is trityl group or THP, the deprotection can be effected by treating with an acid. Specifically, by using p-toluenesulfonic acid as an acid, the reaction can be effected in a solvent such as ethanol at a temperature of room temperature to the reflux temperature of the solvent, thereby attaining the aimed object.

Compound (I-2) ($A=R^1$, $B=\text{—}(CH_2)n\text{-}NR^2R^3$, $Z=\text{—}O\text{—}$)

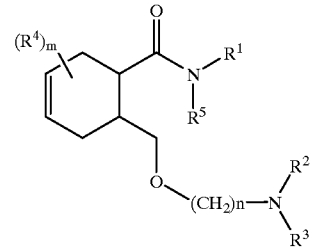

(I-2)

Figure 7:
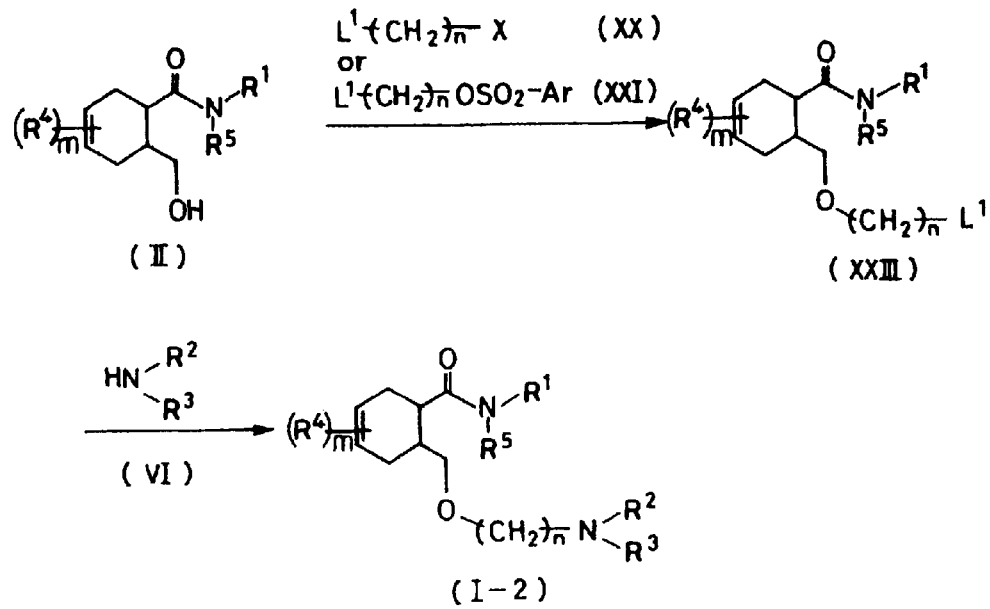

Compound (I-2) of the present invention can be synthesized as shown in Reaction Formula BA of FIG. 7. Namely, a hydroxyl group of Compound (II) is alkylated and then the produced Compound (XXIII) is reacted with an amine (VI), thereby producing Compound (I-2).

The reaction at the first step in Reaction Formula BA can be effected by substitution reaction of Compound (II) with a halide (XX) or a sulfonate (XXI).

In the substitution reaction with the halide (XX), Compound (II) is converted into its corresponding alkoxide by using metallic sodium, sodium hydride or the like and then the alkoxide is reacted with the halide (XX). Also, Compound (II) can be reacted with halide (XX) in the presence of a base directly. As a base, sodium amide, potassium carbonate, sodium hydroxide, barium oxide, silver oxide, or the like can be used. As a solvent, an aromatic compound such as benzene, toluene, or xylene; an ether such as tetrahydrofuran or 1,4-dioxane; an amide such as N,N-dimethylformamide, N,N-dimethylacetamide or hexamethylphosphorylamide; acetonitrile; dimethyl sulfoxide; or the like can be used. While the reaction temperature and reaction time may be changed according to the starting materials and the reagents used, the reaction is usually effected at a temperature within the range of 0° C. to the reflux temperature of the solvent. Specifically, for example, Compound (II) is reacted with the halide (XX) in acetone in the presence of potassium carbonate at a temperature within the range of room temperature to the reflux temperature of the solvent, thereby attaining the aimed object.

In the substitution reaction with the sulfonate (XXI), as a solvent, benzene, tetrahydrofuran, 1,4-dioxane, N,N-dimethylformamide, dimethyl sulfoxide, dichloromethane, water or the like can be used. While the reaction temperature and reaction time may be changed according to the starting materials and the reagents used, the reaction is usually effected at a temperature within the range of 0° C. to the reflux temperature of the solvent. The sulfonate (XXI) can be easily synthesized from the corresponding alcohol and p-toluenesulfonyl chloride in the presence of a base such as pyridine. Specifically, for example, a solution of the corresponding alcohol and p-toluenesulfonyl chloride in 1,4-dioxane is added to sodium hydroxide aqueous solution at a temperature within the range of 0° C. to room temperature and then Compound (II) is further added thereto, thereby attaining the aimed object. Ar in the sulfonate (XXI) represents 4-methylphenyl or naphtyl group. The definition of Ar throughout the rest of this specification remains the same.

Also, by using the other ester type compound in place of the sulfonate (XXI) a substitution reaction is effected in the similar manner to this method, thereby obtaining Compound (I-2). For example, a carbonate or a trichloroacetoimidate corresponding to the sulfonate (XXI) can be used therefor.

The reaction at the second step of Reaction Formula BA can be effected according to the second step in Reaction Formula AB.

Figure 8:
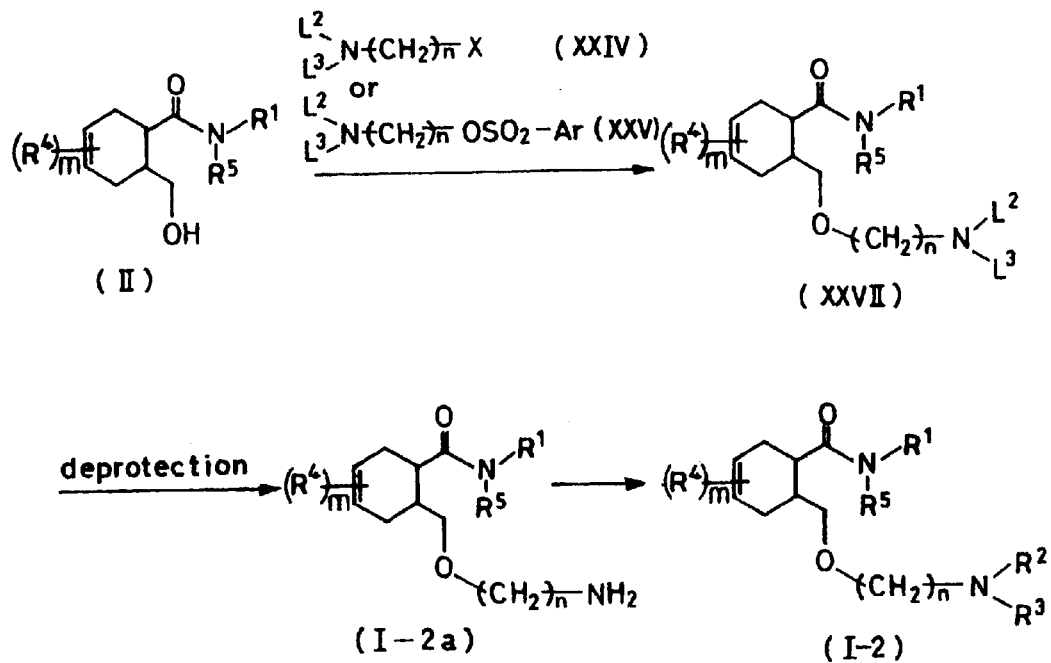

Also, Compound (I-2a) wherein $R^2$ and $R^3$ of Compound (I-2) are hydrogen atoms can be synthesized as shown in Reaction Formula BB of FIG. 8. First, a hydroxyl group of Compound (II) is alkylated to produce Compound (XXVII). Then, Compound (XXVII) is deprotected, thereby producing Compound (I-2a). The alkylation at the first step in Reaction Formula BB can be effected according to the first step in Reaction Formula BA. The deprotection at the second step of Reaction Formula BB can be effected according to the second step in Reaction Formula AC. Further, in the similar manner to Reaction Formula AD, Compound (I-2a) can be converted into Compound (I-2).

Compound (I-3) ($A=R^1$, $B=-(CH_2)n-NR^2R^3$, $Z=-OCO-$)

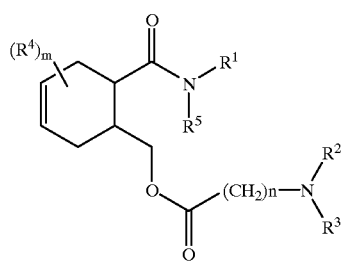

(I-3)

Figure 9:
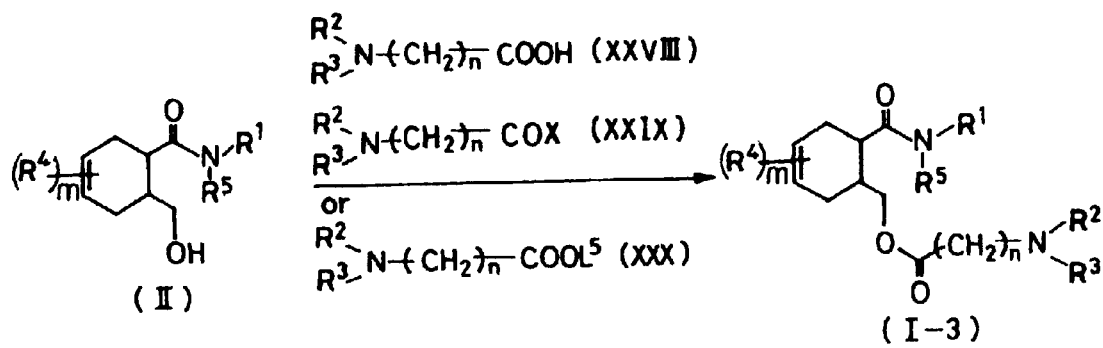

Compound (I-3) of the present invention can be synthesized by acylating a hydroxyl group of Compound (II) as shown in Reaction Formula CA of FIG. 9. This reaction can be effected by a dehydrating condensation reaction of Compound (II) with a carboxylic acid (XXVIII), a reaction with an acid halide (XXIX), an ester interchange reaction with an ester (XXX), or the like.

As for the dehydrating condensation reaction with the carboxylic acid (XXVIII), a method that the both compounds are directly reacted usually in the presence of an acidic catalyst, a method that the carboxylic acid (XXVIII) is converted into its active ester and then the active ester is reacted with Compound (II), or the like can be used. In the former method, as an acidic catalyst, a mineral acid such as hydrochloric acid, sulfuric acid, or boric acid, an organic acid such as aromatic sulfonic acid, a Lewis acid such as boron trifluoride, or the like can be used. As a solvent, an aromatic compound such as benzene, toluene, or xylene; an ether such as tetrahydrofuran or 1,4-dioxane; an amide such as N,N-dimethylformamide or N,N-dimethylacetamide; a halogenated hydrocarbon such as dichloromethane or dichloroethane; or the like can be used. While the reaction temperature and reaction time may be changed according to the starting materials and the reagents used, the reaction is usually effected at a temperature within the range of 0° C. to the reflux temperature of the solvent. Specifically, for example, concentrated sulfuric acid is added to a solution of Compound (II) and the carboxylic acid (XXVIII) in dichloroethane and then the reaction is effected at a temperature within the range of room temperature to the reflux temperature of the solvent, thereby attaining the aimed object. Also, a mixture of Compound (II), the carboxylic acid (XXVIII) and boron trifluoride is reacted at a temperature within the range of room temperature to the reflux temperature of the solvent, thereby attaining the aimed object.

In the latter method proceeding by way of the active ester of the carboxylic acid (XXVIII), by using trifluoroacetic acid anhydride, N,N-dicyclohexylcarbodiimide (DCC) or the like, the carboxylic acid (XXVIII) is converted into its corresponding active ester and then the active ester is reacted with Compound (II). As a solvent, benzene, tetrahydrofuran, N,N-dimethylformamide, dichloromethane or the like can be used. While the reaction temperature and reaction time may be changed according to the starting materials and the reagents used, the reaction is usually effected at a temperature within the range of 0° C. to the reflux temperature of the solvent. Specifically, for example, trifluoroacetic acid anhydride is added to a solution of the carboxylic acid (XXVIII) in benzene at a temperature within the range of 0° C. to room temperature to convert the carboxylic acid (XXVIII) into its active ester and then the latter is reacted with Compound (II), thereby attaining the aimed object.

The reaction with the acid halide (XXIX) can be usually effected in the presence of a base. As a base, for example, an inorganic base such as sodium hydroxide or potassium hydroxide; or an organic base such as pyridine, dimethylaniline, or triethylamine can be used. As a solvent, benzene, tetrahydrofuran, 1,4-dioxane, N,N-dimethylformamide, or the like can be used. While the reaction temperature and reaction time may be changed according to the starting materials and the reagents used, the reaction is usually effected at a temperature within the range of 0° C. to the reflux temperature of the solvent. Specifically, for example, the acid halide (XXIX) is added to a solution containing Compound (II) and pyridine in dichloromethane and then the reaction is effected at a temperature within the range of 0° C. to room temperature, thereby attaining the aimed object. Also, sodium hydroxide aqueous solution is dropwise added to a mixture of Compound (II) and acid halide (XXIX), thereby attaining the aimed object.

In the ester interchange reaction with the ester (XXX), as a catalyst, an acid such as sulfuric acid or p-toluenesulfonic acid, or a base such as potassium alkoxide or titanium (IV) alkoxide can be used. The reaction can be effected with or without a solvent. In this reaction, it is preferable that either Compound (II) or the ester (XXX) is used excessively, or that an alcohol $L^5OH$ produced during the reaction is removed from the reaction system. As a solvent, benzene, toluene, tetrahydrofuran, 1,4-dioxane, N,N-dimethylformamide, dichloromethane or the like can be used. While the reaction temperature and reaction time may be changed according to the starting materials and the reagents used, the reaction is usually effected at a temperature within the range of 0° C. to 200° C. and, preferably, room temperature to the reflux temperature of the solvent. Specifically, for example, titanium(IV) alkoxide is added to a solution containing Compound (II) and the ester (XXX) in benzene and then the reaction is effected at a temperature within the range of room temperature to the reflux temperature of the solvent, thereby attaining the aimed object. As for $L^5$ of the ester (XXX), any of groups can be used if they form esters usually used for this ester interchange reaction. Examples of $L^5$ include an alkyl group such as methyl or ethyl group. The definition of $L^5$ throughout the rest of this specification remains the same.

Figure 10:
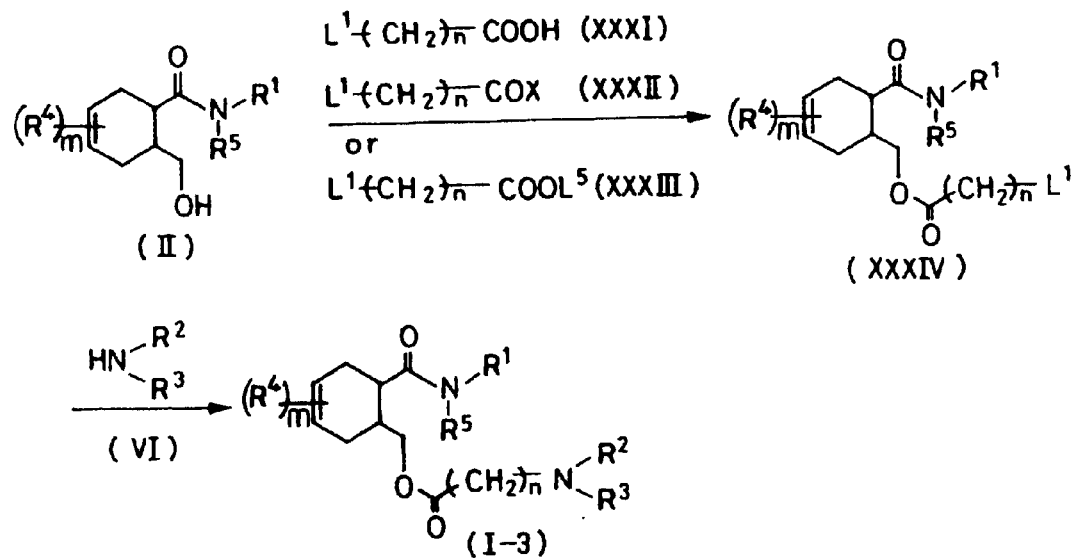

Also, Compound (I-3) can be synthesized as shown in Reaction Formula CB of FIG. 10. First, a hydroxyl group of Compound (II) is acylated to produce Compound (XXXIV). Then, Compound (XXXIV) is reacted with the amine (VI), thereby producing Compound (I-3). The first step in this Reaction Formula CB can be effected according to Reaction Formula CA. The second step can be effected according to the second step in Reaction Formula AB.

Figure 11:
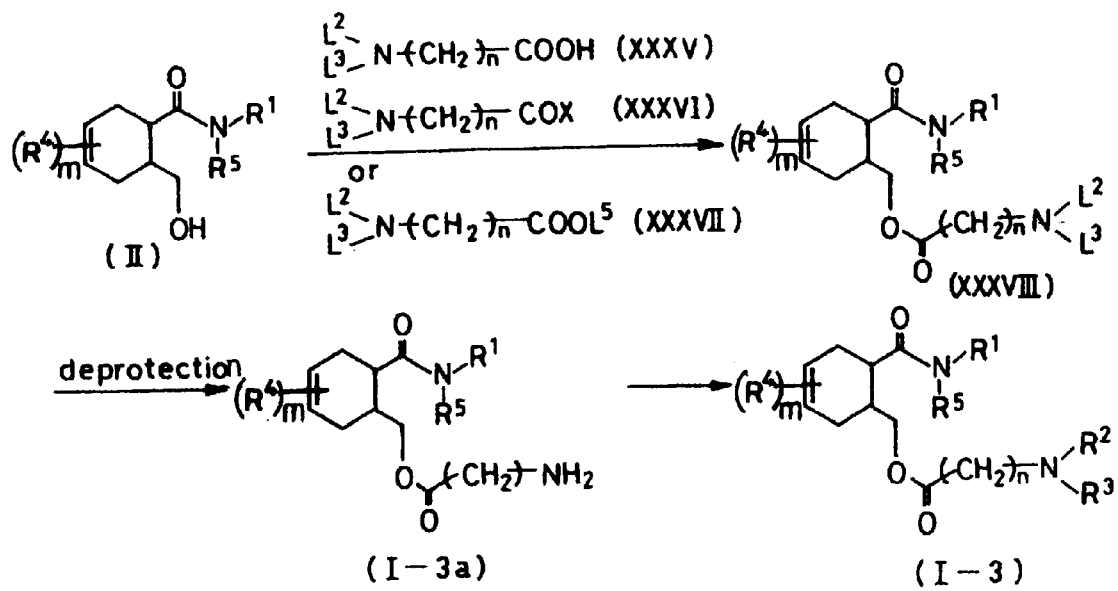

Also, Compound (I-3a) wherein $R^2$ and $R^3$ of Compound (I-3) are hydrogen atoms can be synthesized as shown in Reaction Formula CC of FIG. 11. First, a hydroxyl group of Compound (II) is acylated to produce Compound (XXXVIII). Then, Compound (XXXVIII) is deprotected, thereby producing Compound (I-3a). The acylation reaction at the first step in Reaction Formula CC can be effected according to Reaction Formula CA. The deprotection at the second step in Reaction Formula CC can be effected according to the second step in Reaction Formula AC. Further, in the similar manner to Reaction Formula AD, Compound (I-3a) can be converted into Compound (I-3).

Compound (I-4) ($A=R^1$, $B=$—$(CH_2)n$-$NR^2R^3$, $Z=$—$NR^6$—)

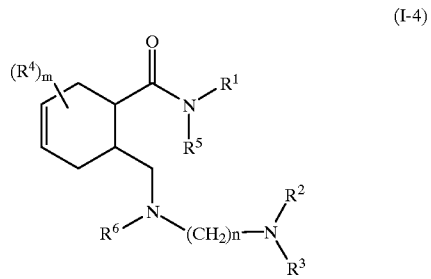

(I-4)

Figure 12:
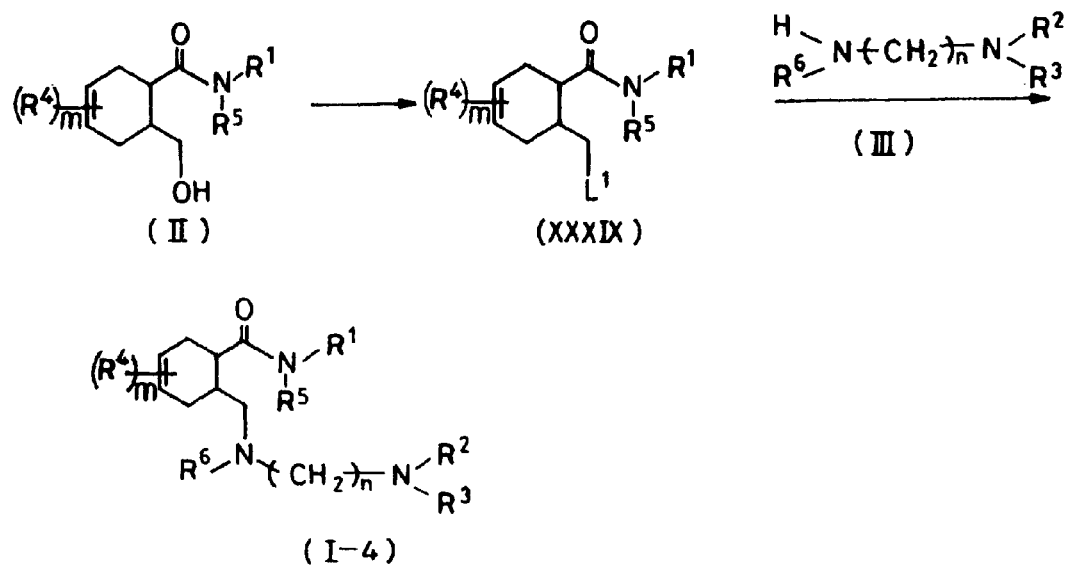

Compound (I-4) of the present invention can be synthesized as shown in Reaction Formula DA in FIG. 12. Namely, a hydroxyl group of Compound (II) is substituted with $L^1$, wherein $L^1$ is an atom or a group which can be easily substituted with nitrogen atom, to produce Compound (XXXIX). Then, Compound (XXXIX) is reacted with an amine (III), thereby producing Compound (I-4).

At the first step in Reaction Formula DA, when $L^1$ is a halogen atom, phosphorus pentachloride, phosphorus trichloride, thionyl chloride or the like can be used therefor. As an additive, for example, an organic base such as triethylamine, pyridine or N-methylmorpholine can be used. As a solvent, for example, a halogenated hydrocarbon such as dichloromethane or chloroform; an aromatic compound such as benzene, toluene, xylene, or pyridine; an ether such as diethyl ether, tetrahydrofuran or 1,4-dioxane; an amide such as N,N-dimethylformamide or N,N-dimethylacetamide; an sulfoxide such as dimethyl sulfoxide; or a mixed solvent thereof can be used. While the reaction temperature and reaction time may be changed according to the starting materials and the reagents used, the reaction is usually effected at a temperature within the range of 0° C. to the reflux temperature of the solvent.

When $L^1$ is a group such as tosyloxy or mesyloxy, the reaction can be effected by reacting Compound (II) with p-toluenesulfonyl chloride, methanesulfonyl chloride, or the like in the presence of a base such as pyridine. Specifically, for example, a solution containing Compound (II) and p-toluenesulfonyl chloride in 1,4-dioxane is added to sodium hydroxide aqueous solution at a temperature within the range of 0° C. to room temperature, thereby attaining the aimed object.

The second step in Reaction Formula DA can be effected according to the second step in Reaction Formula AB.

Figure 13:
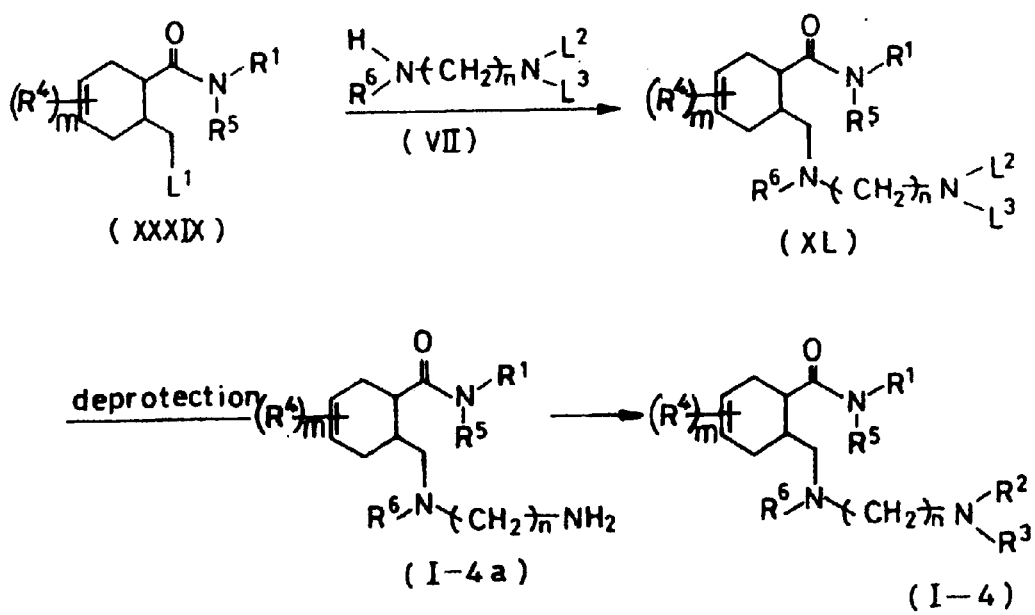

Also, Compound (I-4a) wherein $R^2$ and $R^3$ of Compound (I-4) are hydrogen atoms can be synthesized as shown in Reaction Formula DB of FIG. 13. First, Compound (XXXIX) is reacted with the amine (VII) to produce Compound (XL). Then, Compound (XL) is deprotected, thereby producing Compound (I-4a). The first step of Reaction Formula DB can be effected according to at the second step in Reaction Formula DA. The deprotection at the second step of Reaction Formula DB can be effected according to the second step in Reaction Formula AC. Further, in the similar manner to Reaction Formula AD, Compound (I-4a) can be converted into Compound (I-4).

A compound wherein $R^5$ of the intermediate (XXXIX) in Reaction Formula DA is a lower alkyl, lower acyl, or lower alkylcarbamoyl group also can be synthesized as follows. Namely, a hydroxyl group of Compound (XIV) obtained by Reaction Formula AE is converted into $L^1$ and then $R^{5'}$ is introduced therefor to produce the compound. The former reaction can be effected according to the first step in Reaction Formula DA. The later reaction can be effected according to the second step in Reaction Formula AF.

Compound (I-5) ($A=$—$(CH_2)n$-$NR^2R^3$, $B=R^1$, $Z=$—$OCONR^6$—)

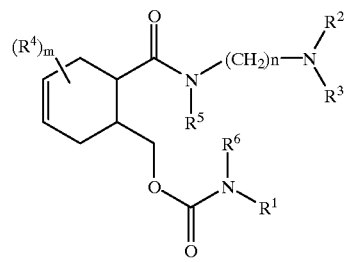

(I-5)

Figure 14:
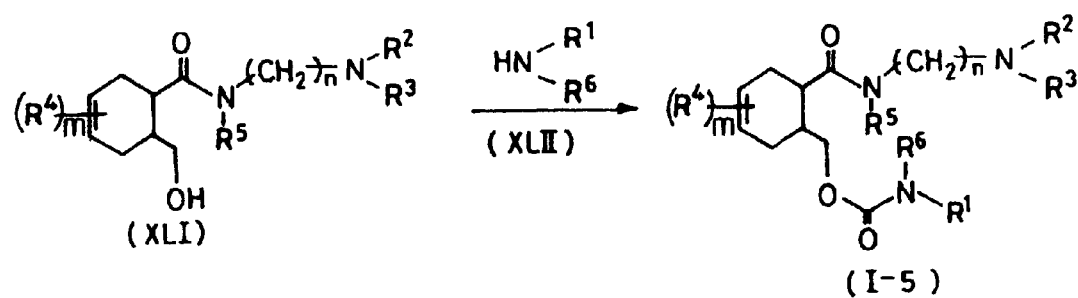

Compound (I-5) of the present invention can be synthesized from Compound (XLI) and an amine (XLII) as shown in Reaction Formula EA of FIG. 14. This reaction can be effected according to Reaction Formula AA.

Figure 15:
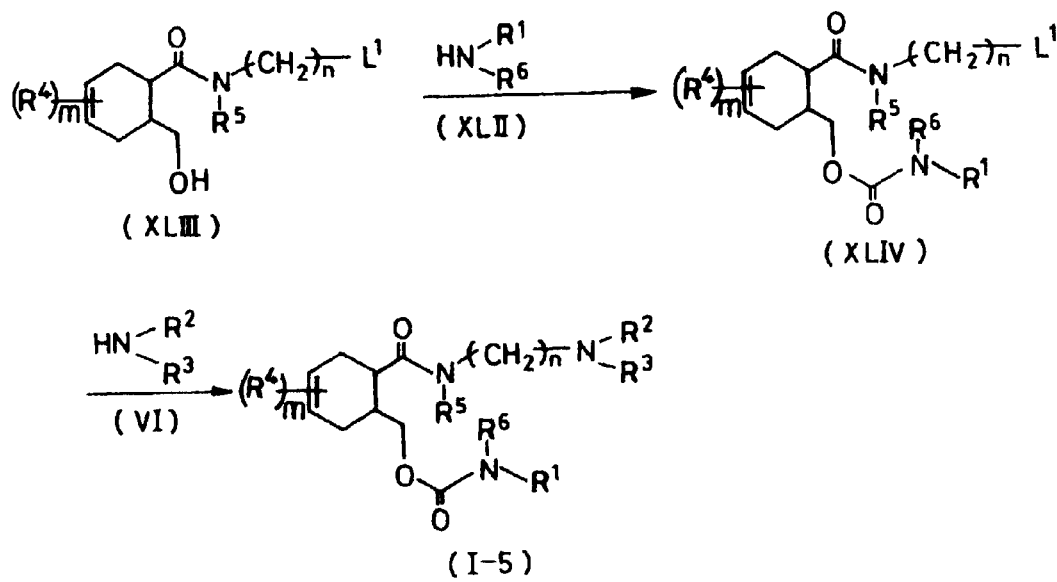

Also, Compound (I-5) can be synthesized as shown in Reaction Formula EB of FIG. 15. First, Compound (XLIV) is synthesized from Compound (XLIII) and the amine (XLII). Then, Compound (XLIV) is reacted with the amine (VI) to produce Compound (I-5).

The first step in Reaction Formula EB can be effected according to Reaction Formula AA. The second step in Reaction Formula EB can be effected according to the second step in Reaction Formula AB.

Figure 16:
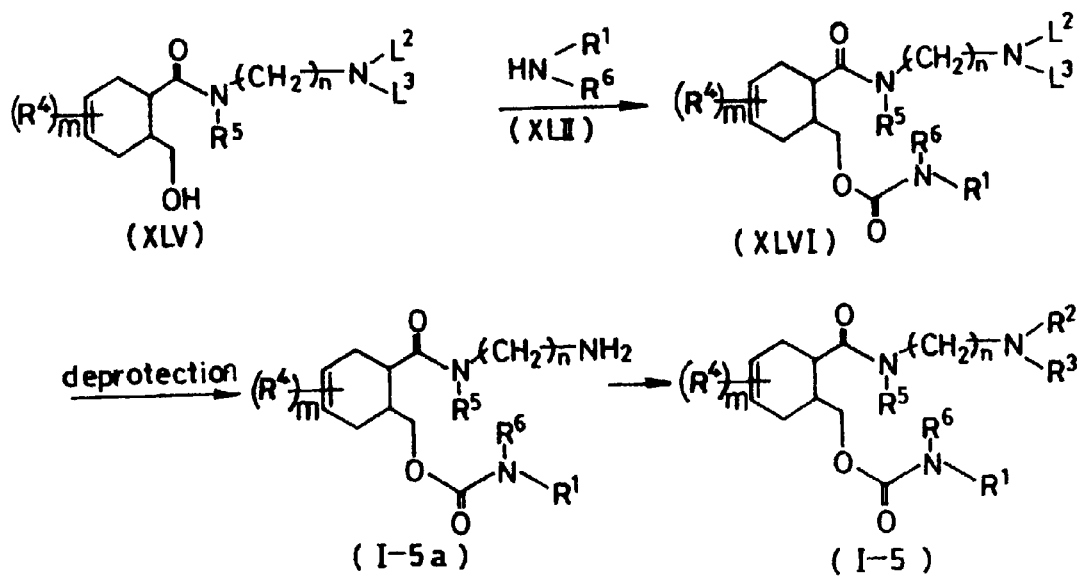

Also, Compound (I-5a) wherein $R^2$ and $R^3$ of Compound (I-5) are hydrogen atoms can be synthesized as shown in Reaction Formula EC of FIG. 16. First, Compound (XLVI) is synthesized from Compound (XLV) and the amine (XLII). Then, Compound (XLVI) is deprotected, thereby producing Compound (I-5a). The first step in Reaction Formula EC can be effected according to Reaction Formula AA, respectively. The deprotection at the second step of Reaction Formula EC can be effected according to the second step in Reaction Formula AC. Further, in the similar manner to Reaction Formula AD, Compound (I-5a) can be converted into Compound (I-5).

The starting material (XLI), (XLIII) or (XLV) can be synthesized when reactions is effected in the similar manner to Reaction Formulae AE to AF by using an amine of $H_2N—(CH_2)n-NR^2R^3$, $H_2N—(CH_2)n-L^1$ and $H_2N—(CH_2)n-NL^2L^3$ in the place of the amine (XII) in Reaction Formula AE.

Compound (I-6) (A=—$(CH_2)n-NR^2R^3$, B=$R^1$, Z=—O—)

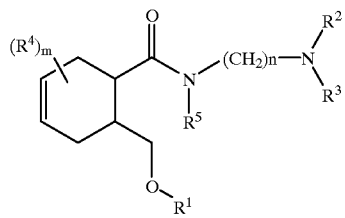

(I-6)

Figure 17:
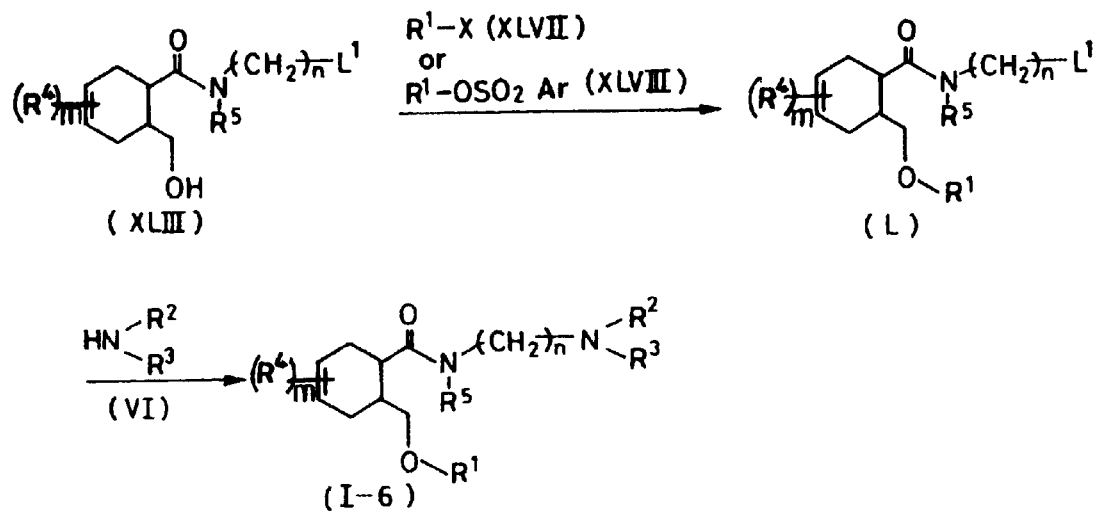
Figure 18:
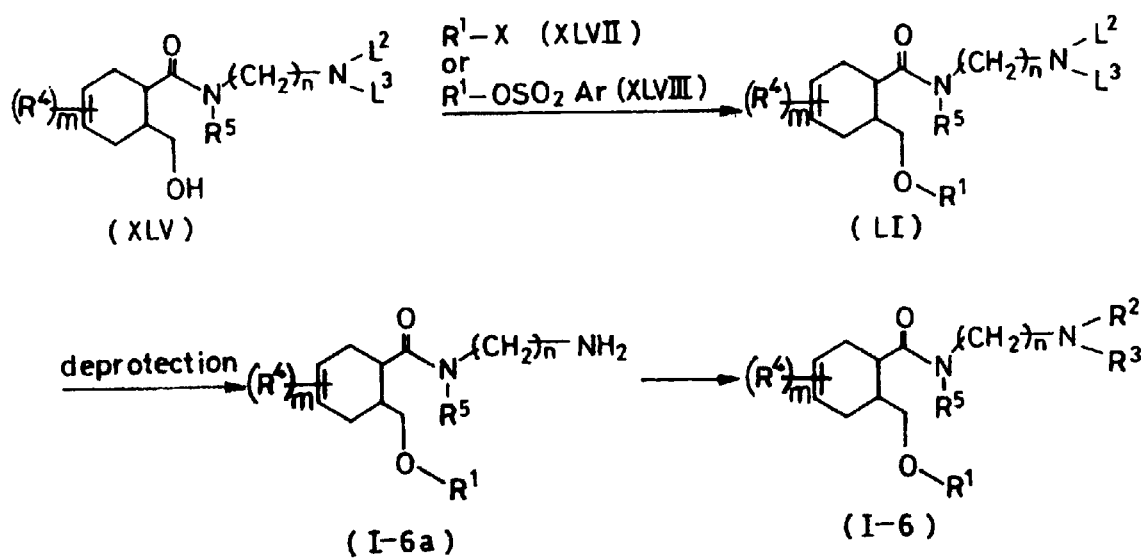

Compound (I-6) of the present invention can be synthesized as shown in Reaction Formula FA or FB of FIG. 17 or 18. These Reaction Formulae can be effected according to Reaction Formulae BA and BB, respectively.

Compound (I-7) (A=—$(CH_2)n-NR^2R^3$, B=$R^1$, Z=—OCO—)

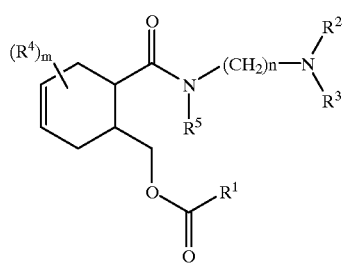

(I-7)

Figure 19:
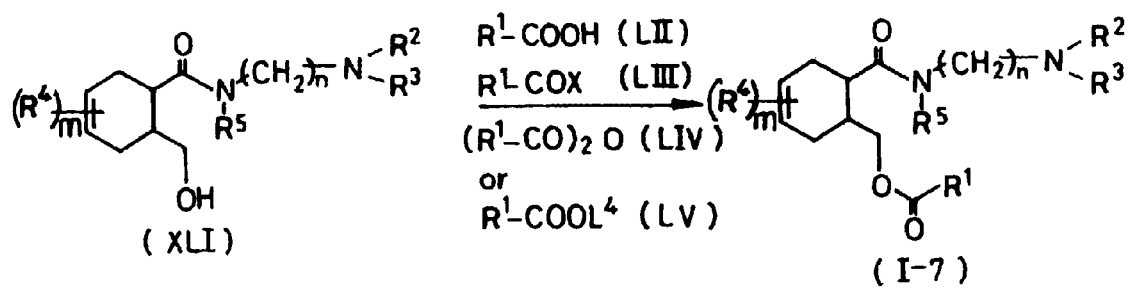
Figure 20:
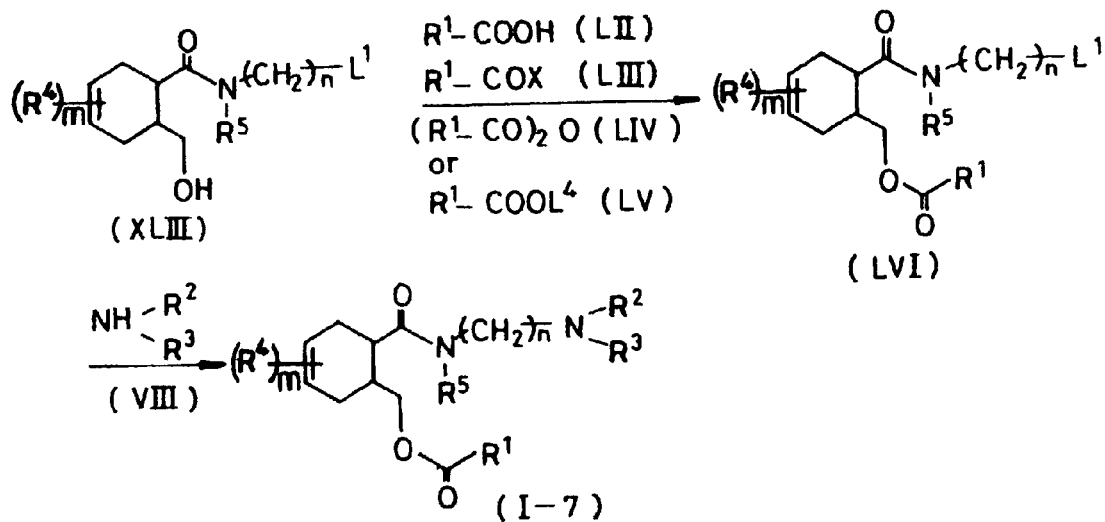
Figure 21:
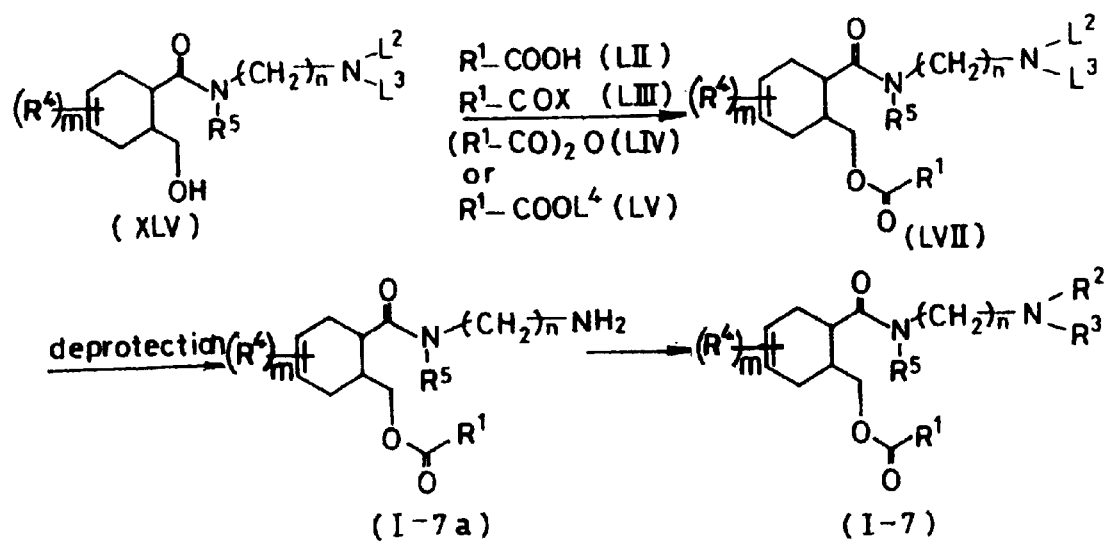

Compound (I-7) of the present invention can be synthesized as shown in Reaction Formulae GA to GC in FIGS. 19 to 21. These Reaction Formulae can be effected according to Reaction Formulae CA to CC, respectively.

The method using an acid anhydride (LIV) can be effected in the similar manner to the case using an acid halide (LIII).

Compound (I-8) (A=—$(CH_2)n-NR^2R^3$, B=$R^1$, Z=—$NR^6$—)

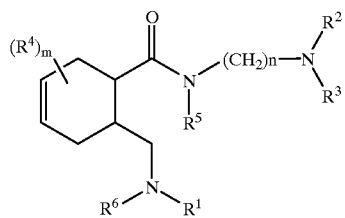

(I-8)

Figure 22:
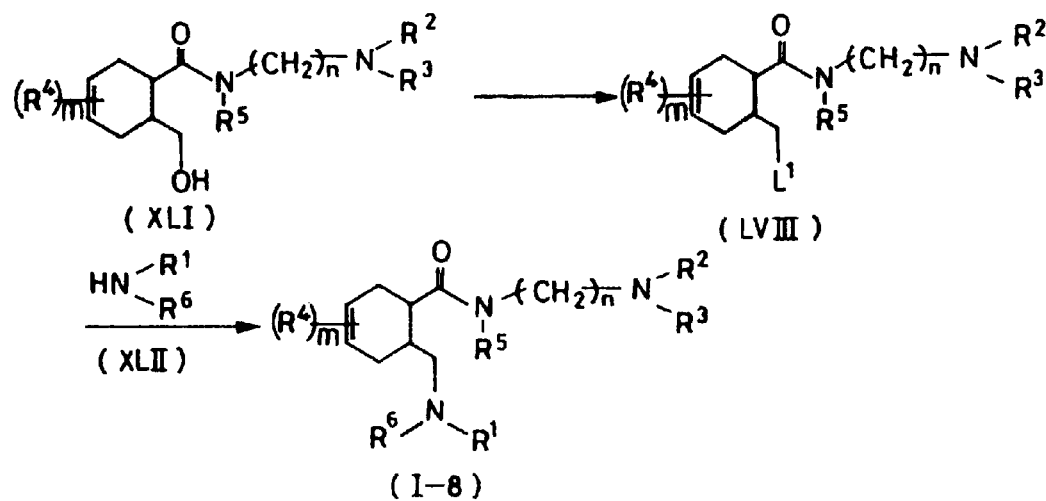
Figure 23:
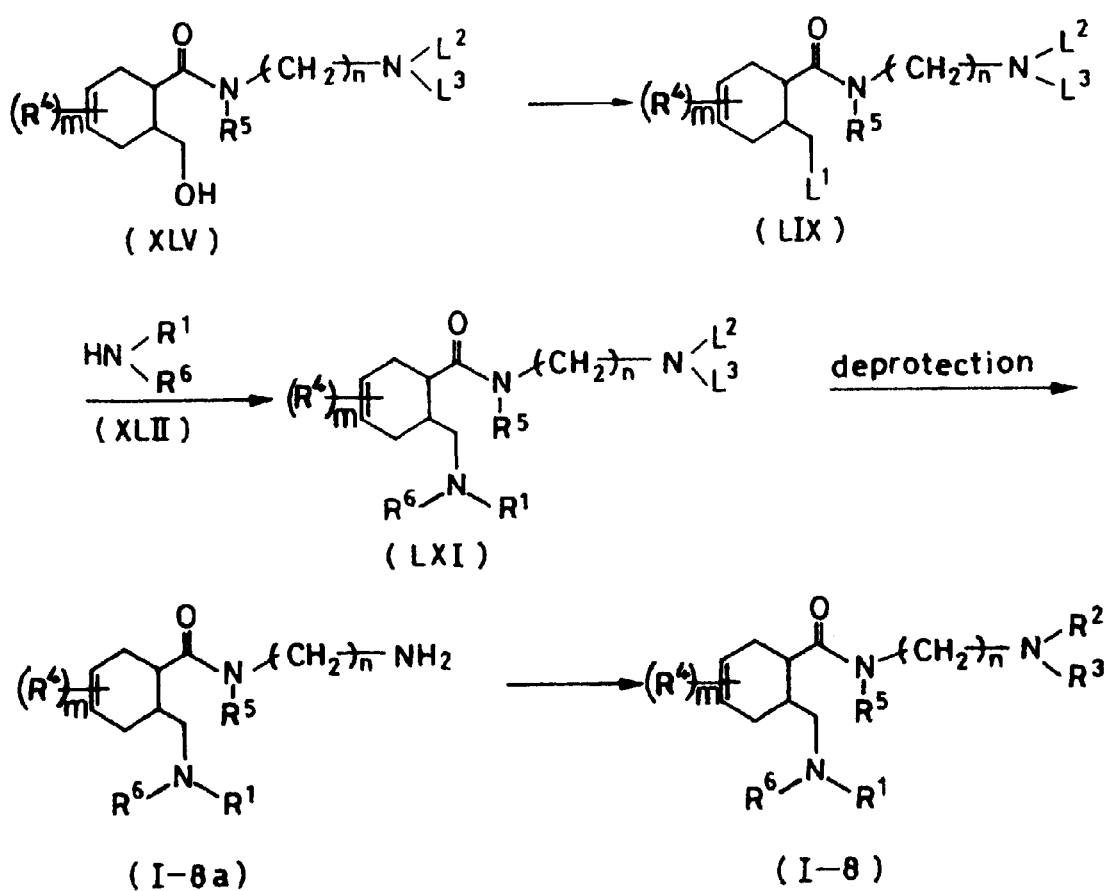

Compound (I-8) of the present invention can be synthesized as shown in Reaction Formula HA or HB of FIG. 22 or 23.

Reaction Formula HA can be effected according to Reaction Formula DA.

The first and second steps of Reaction Formula HB can be effected according to the first and second steps in Reaction Formula DA, respectively. The deprotection at the third step in Reaction Formula HB can be effected according to the second step in Reaction Formula AC. Also, in the similar manner to Reaction Formula AD, Compound (I-8a) wherein $R^2$ and $R^3$ are hydrogen atoms can be converted into Compound (I-8).

Figure 24:
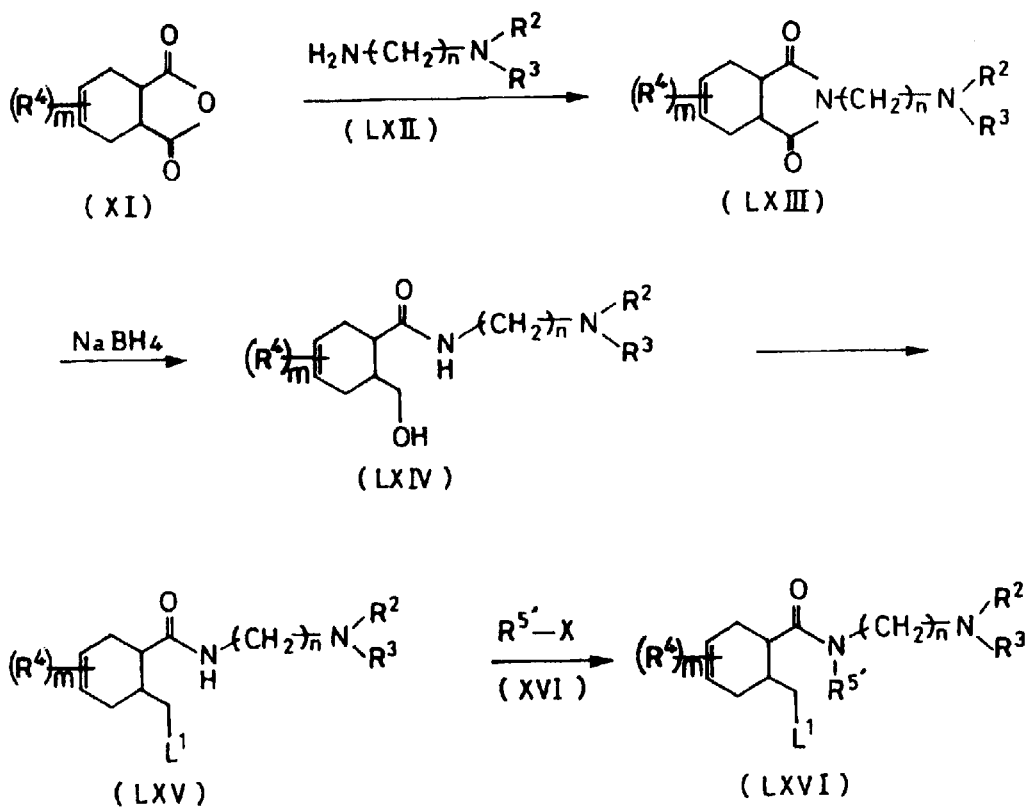
FIG. 24 shows an example of steps for manufacturing an intermediate of [6-(substituted-methyl)-3-cyclohexenyl] formamide derivative in accordance with the present invention.

Compound (LXVI) wherein $R^5$ of the intermediate (LVIII) in Reaction Formula HA is a lower alkyl, lower acyl, or lower alkylcarbamoyl group also can be synthesized as shown in Reaction Formula HC of FIG. 24. Namely, Compound (LXIV) is synthesized from Compound (XI) by a reaction according to Reaction Formula AE. Then, reactions according to the first step of Reaction Formula DA and the second step of Reaction Formula AF are effected successively, thereby producing Compound (LXVI).

Also, a compound wherein $R^5$ of the intermediate (LIX) in Reaction Formula HB is a lower alkyl, lower acyl, or lower alkylcarbamoyl group can be synthesized when a reaction is effected in the similar manner to Reaction Formula HC except for using an amine $H_2N—(CH_2)n-NL^2L^3$ in the place of the amine (LXII).

Figure 25:
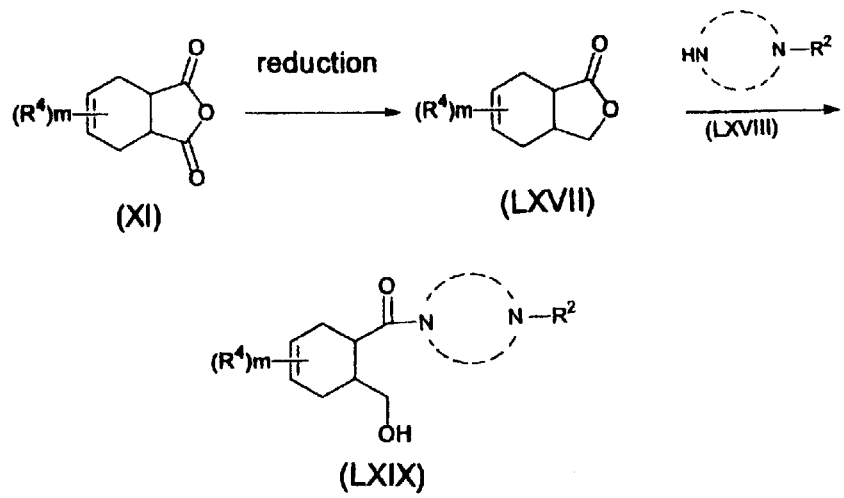

A compound wherein —$CONR^5—(CH_2)n-NR^2R^3$ in each of formulae (I-5) to (I-8) is —CO—W can be produced from Compound (LXIX) by the reactions according to the above-mentioned Reaction Formulae. Compound (LXIX) can be synthesized as shown in Reaction Formula IA of FIG. 25.

In Reaction Formula IA, Compound (XI) is reduced and then reacted with an amine (LXVIII), thereby producing Compound (LXIX).

In the reaction at the first step, as an reducing agent, for example, sodium borohydride, lithium aluminum hydride, ruthenium chloride or the like can be used. As a solvent, an aromatic hydrocarbon such as benzene, toluene, or xylene; an ether such as tetrahydrofuran or 1,4-dioxane; an alcohol such as ethanol or 2-propanol; or the like can be used. While the reaction temperature and reaction time may be changed according to the starting materials and the reducing agents used, the reaction is usually effected at a temperature within the range of −78° C. to the reflux temperature of the solvent. Specifically, for example, Compound (XI) is added to a solution of sodium borohydride in 2-propanol and the reaction is effected at a temperature within the range of room temperature to the reflux temperature of the solvent, thereby attaining the aimed object.

The reaction with the amine (LXVIII) at the second step can be effected with or without a solvent. As a solvent, a halogenated hydrocarbon such as dichloromethane or chloroform; an aromatic hydrocarbon such as benzene, toluene, or xylene; an ether such as tetrahydrofuran or 1,4-dioxane; an amide such as N,N-dimethylformamide or N,N-dimethylacetamide; a sulfoxide such as dimethyl sulfoxide; or the like can be used. While the reaction temperature and reaction time may be changed according to the starting materials used, the reaction is usually effected at a temperature within the range of room temperature to 150° C. Preferably, this reaction may be effected without a solvent at a temperature of room temperature to 100° C.

Among the starting materials used in the foregoing Reaction Formulae, materials which are not described above are commercially available or can be easily synthesized from a suitable starting material by using known methods.

The [6-(substituted-methyl)-3-cyclohexenyl]formamide derivative (I) provided in the present invention can be changed to an acid-added salt if necessary. Examples of the acid-added salt include salt with an inorganic acid such as hydrochloric acid, hydrobromic acid, sulfuric acid or phosphoric acid and salts with an organic acid such as acetic acid, propionic acid, citric acid, lactic acid, oxalic acid, maleic acid, fumaric acid, succinic acid, tartaric acid or methanesulfonic acid. These salts can be easily manufactured by common methods.

The [6-(substituted-methyl)-3-cyclohexenyl]formamide derivatives in accordance with the present invention, which mechanism of action has not been made clear, have an excellent hair growth and regrowth promoting effect. Accordingly, by applying the compound on skin of mammals such as human scalp, care, improvement, or prevention of hair loss can be expected.

The [6-(substituted-methyl)-3-cyclohexenyl]formamide derivative of the present invention can apply to pathological alopecia such as alopecia areata, alopecia pityrodes or alopecia seborrheica in addition to thin hair or hair loss what is called male pattern baldness or androgenic alopecia. The dosage of the [6-(substituted-methyl)-3-cyclohexenyl]formamide derivative in accordance with the present invention must be determined suitably according to sex, age and degree of symptom in hair loss or thin hair. Usually 0.01–20 mg/cm$^2$ is applied on scalp per day for an adult in a single dose or several doses.

When the [6-(substituted-methyl)-3-cyclohexenyl]formamide derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical forms include tonic, lotion, milky lotion, cream, ointment, gel, spray and mousse.

In addition to the [6-(substituted-methyl)-3-cyclohexenyl]formamide derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin $B_6$.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, rosmarinus officinalis, drynaria, cytisus scoparius, gentiana, salviae miltiorrhizeae radix, sponge gourd, platycodon, pinus, sophora root, Japanese angelica root, safflower, Japanese barberry, areca, eucalyptus, prunella spike, akebia stem, achyranthes root, bupleurum root, tea, licorice, hop, Chrysanthemum, senega, sesame, cnidium rhizome, cashew, pueraria root, rosae rugosae flos, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives; lactic acid and its alkyl ester; an organic acid such as citric acid; a protease inhibitor such as tranexamic acid; and the like can be compounded.

Further, an alcohol such as ethanol or isopropyl alcohol; a polyvalent alcohol such as glycerine, propylene glycol or polyethylene glycol; an oily ingredient such as higher fatty acids, higher alcohols, hydrogenated castor oils, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

Hair Regrowth Test (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the tested compound was applied on the shaved portion once a day. For hair regrowth effect of the tested compound, the hair regrowth area of mice's region of back was measured and ratio of the hair regrowth area with respect to the shaved area was evaluated as hair regrowth area rate (%).

(2) Result

Hair regrowth area rates after the following tested compounds were applied for 23–25 days are shown in TABLE 1.

Compound 1

[6-[[N-[3-(Dimethylamino)propyl]carbamoyloxy]methyl]-3-cyclohexenyl]-N-octadecylformamide

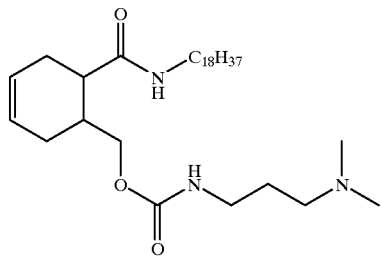

Compound 2

[6-[[N-[3-(Dimethylamino)propyl]carbamoyloxy]methyl]-3-cyclohexenyl]-N-octadecylformamide hydrochloride

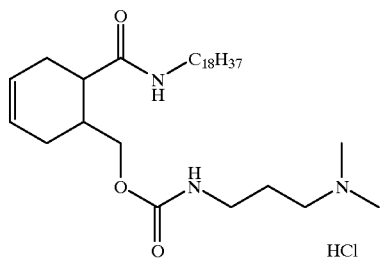

Compound 3

[6-[[N-(3-Morpholinopropyl)carbamoyloxy]methyl]-3-cyclohexenyl]-N-octadecylformamide

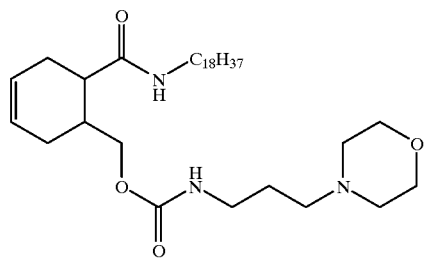

Compound 4

[6-[[N-(3-Morpholinopropyl)carbamoyloxy]methyl]-3-cyclohexenyl]-N-octadecylformamide hydrochloride

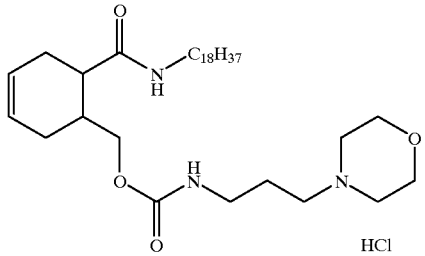

Compound 5

{6-[(Octadecylamino)carbonyl]-3-cyclohexenyl}methyl 4-methyltetrahydro-1(2H)-pyrazinecarboxylate

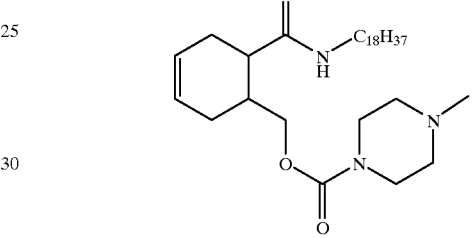

Compound 6

{6-[(Octadecylamino)carbonyl]-3-cyclohexenyl}methyl 4-methyltetrahydro-1(2H)-pyrazinecarboxylate hydrochloride

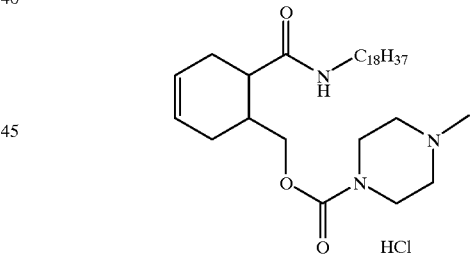

TABLE 1

| Compound | Conc. of Compd. (w/v %) | Days of Application (days) | Hair Regrowth Area Rate (%) |
|---|---|---|---|
| Ethanol (negative contrast) | — | 25 | 0 |
| Compound 1 | 0.1 | 24 | 96 |
| Compound 2 | 0.1 | 24 | 95 |
| Compound 3 | 0.1 | 25 | 100 |
| Compound 4 | 0.1 | 23 | 100 |
| Compound 5 | 0.1 | 25 | 100 |
| Compound 6 | 0.1 | 24 | 100 |

As is clear from the TABLE 1, [6-(substituted-methyl)-3-cyclohexenyl]formamide derivatives and their pharmacologically acceptable salts in accordance with the present invention show excellent hair regrowth and growth promoting effects.

In the following, examples of compounds and compositions in accordance with the present invention will be explained. However, the present invention should not be restricted thereto.

Example 1

[6-[[N-[3 -(Dimethylamino)propyl]carbamoyloxy] methyl]-3-cyclohexenyl]-N-octadecylformamide (Compound 1)

(1) 2-Octadecyl-4,7,3a,7a-tetrahydroisoindole-1,3-dione

Octadecylamine (5.31 g) was added to 4,7,3a,7a-tetrahydroisobenzofuran-1,3-dione (3.00 g). After being stirred for 2 hours at 110° C., the reaction mixture was purified by silica gel column chromatography (silica gel 80 g, chloroform), thereby yielding the entitled compound (7.85 g) as yellow crystals.

$^1$H-NMR (CDCl$_3$) δ:0.88 (3H, t, J=6.8 Hz), 1.2–1.35 (30H, m), 1.51 (2H, m), 2.22 (2H, m), 2.61 (2H, m), 3.05 (2H, m), 3.45 (2H, t, J=7.3 Hz), 5.89 (2H, m).

(2) [6-(Hydroxymethyl)-3-cyclohexenyl]-N-octadecylformamide

2-Octadecyl-4,7,3a,7a-tetrahydroisoindole-1,3-dione (5.00 g) was suspended into a mixture of 2-propanol (90 ml) and water (15 ml) and then sodium borohydride (2.34 g) was added thereto. After being stirred for 46 hours at room temperature, the reaction mixture was acidified with dilute hydrochloric acid and then concentrated. The residue was, with chloroform added thereto, washed with dilute hydrochloric acid, water and saturated sodium hydrogencarbonate aqueous solution successively, dried over sodium sulfate anhydride, and concentrated. The residue was purified by silica gel column chromatography (silica gel 80 g, chloroform:methanol=50:1–10:1), thereby yielding the entitled compound (4.32 g) as white crystals.

$^1$H-NMR (CDCl$_3$) δ:0.88 (3H, t, J=6.8 Hz), 1.2–1.35 (30H, m), 1.48 (2H, m), 1.85 (1H, m), 2.10–2.42 (4H, m), 2.84 (1H, m), 3.19 (1H, ddd, J=20.0, 7.3, 5.9 Hz), 3.29 (1H, ddd, J=20.0, 7.3, 5.9 Hz), 3.52 (1H, brs), 3.62 (2H, m), 5.76 (2H, m), 5.99 (1H, brt).

(3) [6-[[N-[3-(Dimethylamino)propyl] carbamoyloxy]methyl]-3-cyclohexenyl]-N-octadecylformamide Pyridine (0.47 ml) and phenyl chlorocarbonate (0.54 ml) were added to a suspension of [6-(hydroxymethyl)-3-cyclohexenyl]-N-octadecylformamide (1.58 g) in methylene chloride (15 ml) while being cooled with ice. After being stirred for 1.5 hours at room temperature, the reaction mixture was diluted with chloroform, washed with saturated sodium hydrogencarbonate aqueous solution and water successively, dried over sodium sulfate anhydride, and concentrated. N,N-Dimethyl-1,3-propanediamine (0.54 ml) was added to the residue and stirred for 4 hours at 70° C. The reaction mixture was purified by silica gel column chromatography (silica gel 50 g, chloroform:methanol=20:1–10:1), thereby yielding the entitled compound (1.93 g) as white wax.

$^1$H-NMR (CDCl$_3$) δ:0.88 (3H, t, J=6.8 Hz), 1.2–1.35 (30H, m), 1.49 (2H, m), 1.66 (2H, m), 2.02–2.37 (7H, m), 2.23 (6H, s), 2.66 (1H, m), 3.24 (4H, m), 3.98 (1H, dd, J=10.3, 8.7 Hz), 4.13 (1H, dd, J=10.3, 8.7 Hz), 5.61 (1H, brt), 5.73 (2H, m), 6.22 (1H, brt).

Example 2

[6-[[N-[3-(Dimethylamino)propyl]carbamoyloxy] methyl]-3-cyclohexenyl]-N-octadecylformamide hydrochloride (Compound 2)

4N Hydrochloric acid/ethyl acetate solution (0.19 ml) was added to a solution of [6-[[N-[3-(dimethylamino)propyl] carbamoyloxy]methyl]-3-cyclohexenyl]-N-octadecylformamide (0.20 g) in ethyl acetate (4 ml) while being cooled with ice and then stirred for 10 minutes. The deposited crystals were dissolved in ethanol and concentrated. The residue was crystallized with ethyl acetate, thereby yielding the entitled compound (0.21 g) as white crystals.

$^1$H-NMR (CDCl$_3$) δ:0.88 (3H, t, J=6.8 Hz), 1.2–1.35 (30H, m), 1.49 (2H, m), 2.02–2.40 (7H, m), 2.70 (1H, m), 2.82 (3H, s), 2.83 (3H, s), 3.15 (2H, m), 3.23 (2H, m), 3.36 (2H, m), 4.05 (2H, m), 5.73 (2H, m), 5.93 (1H, brt), 6.14 (1H, brt), 12.06 (1H, brs).

Example 3

[6-[[N-(3-Morpholinopropyl)carbamoyloxy]methyl]-3-cyclohexenyl]-N-octadecylformamide (Compound 3)

Pyridine (0.30 ml) and phenyl chlorocarbonate (0.34 ml) were added to a suspension of [6-(hydroxymethyl)-3-cyclohexenyl]-N-octadecylformamide (1.01 g) in methylene chloride (10 ml) while being cooled with ice. After being stirred for 1 hour at room temperature, the reaction mixture was diluted with chloroform, washed with saturated sodium hydrogencarbonate aqueous solution and water successively, dried over sodium sulfate anhydride, and concentrated. N-(3-Aminopropyl)morpholine (0.40 ml) was added to the residue and stirred for 4 hours at 70° C. The reaction mixture was purified by silica gel column chromatography (silica gel 30 g, chloroform:methanol=50:1), thereby yielding the entitled compound (1.22 g) as white wax.

$^1$H-NMR (CDCl$_3$) δ:0.88 (3H, t, J=6.8 Hz), 1.2–1.35 (30H, m), 1.49 (2H, m), 1.6 (2H, m), 2.02–2.50 (11H, m), 2.65 (1H, m), 3.24 (4H, m), 3.71 (4H, t, J=4.6 Hz), 3.98 (1H, dd, J=10.8, 6.3 Hz), 4.14 (1H, dd, J=10.8, 6.3 Hz), 5.73 (2H, m), 5.76 (1H, brt), 6.28 (1H, brt).

Example 4

[6-[[N-(3-Morpholinopropyl)carbamoyloxy]methyl]-3-cyclohexenyl]-N-octadecylformamide hydrochloride (Compound 4)

4N Hydrochloric acid/ethyl acetate solution (0.26 ml) was added to a solution of [6-[[N-(3-morpholinopropyl) carbamoyloxy]methyl]-3-cyclohexenyl]-N-octadecylformamide (0.30 g) in ethyl acetate (4 ml). After being stirred for 10 minutes at room temperature, the reaction mixture was concentrated. The residue was crystallized with ethyl acetate, thereby yielding the entitled compound (0.26 g) as white crystals.

$^1$H-NMR (CDCl$_3$) δ:0.88 (3H, t, J=6.8 Hz), 1.2–1.35 (30H, m), 1.48 (2H, m), 1.98–2.33 (7H, m), 2.70 (1H, m), 2.90 (2H, m), 3.13 (2H, m), 3.23 (2H, m), 3.35 (2H, m), 3.47 (2H, m), 3.99 (2H, m), 4.01 (1H, dd, J=10.7, 7.3 Hz), 4.08

(1H, dd, J=10.7, 7.3 Hz), 4.29 (2H, m), 5.74 (2H, m), 5.87 (1H, brt), 6.07 (1H, brt), 12.59 (1H, brs).

Example 5

{6-[(Octadecylamino)carbonyl]-3-cyclohexenyl}methyl 4-methyltetrahydro-1(2H)-pyrazinecarboxylate (Compound 5)

Pyridine (3.84 ml) and phenyl chlorocarbonate (4.37 ml) were added to a solution of [6-(hydroxymethyl)-3-cyclohexenyl]-N-octadecylformamide (12.92 g) in methylene chloride (100 ml) while being cooled with ice. After being stirred for 1 hour at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-Methylpiperazine (3.87 ml) was added to the residue and stirred for 14 hours at 70° C. The reaction mixture was purified by silica gel column chromatography (silica gel 200 g, chloroform:methanol=50:1–10:1), thereby yielding the entitled compound (16.43 g) as white solid.

$^1$H-NMR (CDCl$_3$) δ:0.88 (3H, t, J=6.8 Hz), 1.2–1.35 (30H, m), 1.49 (2H, m), 2.05 (1H, m), 2.18–2.43 (8H, m), 2.30 (3H, s), 2.66 (1H, ddd, J=6.8, 6.8, 3.4 Hz), 3.24 (2H, m), 3.49 (4H, t, J=4.9 Hz), 4.02 (1H, dd, J=10.8, 7.8 Hz), 4.19 (1H, dd, J=10.8, 5.9 Hz), 5.72 (1H, m), 5.75 (1H, m), 6.13 (1H, brt).

Example 6

{6-[(Octadecylamino)carbonyl]-3-cyclohexenyl}methyl 4-methyltetrahydro-1(2H)-pyrazinecarboxylate hydrochloride (Compound 6)

4N Hydrochloric acid/ethyl acetate solution (11.5 ml) was added to a solution of {6-[(octadecylamino)carbonyl]-3-cyclohexenyl}methyl 4-methyltetrahydro-1(2H)-pyrazinecarboxylate (16.43 g) in ethyl acetate (150 ml). After being stirred for 10 minutes at room temperature, the reaction mixture was concentrated. The residue was recrystallized with ethyl acetate-ethanol mixed solution, thereby yielding the entitled compound (14.69 g) as white solid.

$^1$H-NMR (CDCl$_3$) δ0.88 (3H, t, J=6.8 Hz), 1.2–1.4 (30H, m), 1.47 (2H, m), 2.02 (1H, m), 2.20–2.35 (3H, m), 2.41 (1H, m), 2.67 (1H, m), 2.76–2.90 (2H, m), 2.80 (3H, d, J=4.9 Hz), 3.24 (2H, m), 3.41 (2H, m), 3.72 (2H, m), 4.0–4.4 (4H, m), 5.75 (2H, m), 5.88 (1H, brt), 13.28 (1H, brs).

Example 7

{6-[(Octadecylamino)carbonyl]-3-cyclohexenyl}methyl 4-benzyltetrahydro-1(2H)-pyrazinecarboxylate (Compound 7)

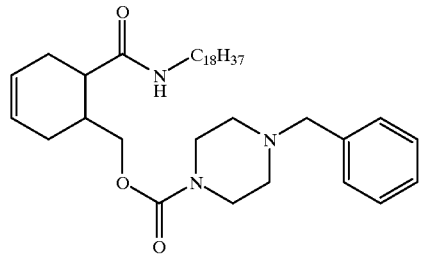

Pyridine (0.72 ml) and phenyl chlorocarbonate (0.82 ml) were added to a solution of [6-(hydroxymethyl)-3-cyclohexenyl]-N-octadecylformamide (2.400 g) in methylene chloride (24 ml) while being cooled with ice. After being stirred for 2.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. 1-Benzylpiperazine (1.14 ml) was added to the residue and stirred for 2 hours at 75° C. The reaction mixture was purified by silica gel column chromatography (silica gel 100 g, chloroform:ethyl acetate=5:1–2:1), thereby yielding the entitled compound (3.219 g) as white solid.

$^1$H-NMR (CDCl$_3$) δ:0.88 (3H, t, J=6.6 Hz), 1.2–1.4 (30H, m), 1.48 (2H, m), 2.05 (1H, m), 2.15–2.45 (4H, m), 2.40 (4H, m), 2.65 (1H, ddd, J=6.8, 6.8, 3.4 Hz), 3.23 (2H, m), 3.47 (4H, t, J=4.9 Hz), 3.51 (2H, s), 4.00 (1H, dd, J=10.8, 7.8 Hz), 4.19 (1H, dd, J=10.8, 5.9 Hz), 5.71 (1H, m), 5.74 (1H, m), 6.14 (1H, t, J=5.4 Hz), 7.24–7.34 (5H, m).

Example 8

{6-[(Octadecylamino)carbonyl]-3-cyclohexenyl}methyl 4-benzyltetrahydro-1(2H)-pyrazinecarboxylate hydrochloride (Compound 8)

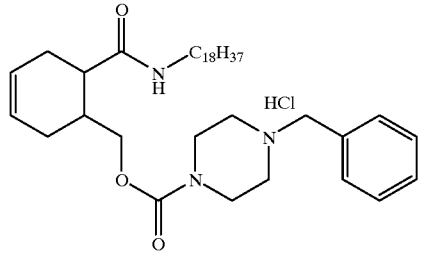

4N Hydrochloric acid/ethyl acetate solution (1.28 ml) was added to a solution of {6-[(octadecylamino)carbonyl]-3-cyclohexenyl}methyl 4-benzyltetrahydro-1(2H)-pyrazine carboxylate (2.600 g) in ethyl acetate (26 ml). After being stirred for half an hour at room temperature, the reaction mixture was concentrated. The residue was recrystallized with ethyl acetate-ethanol mixed solution, thereby yielding the entitled compound (2.412 g) as white solid.

$^1$H-NMR (CDCl$_3$) δ:0.88 (3H, t, J=6.8 Hz), 1.2–1.4 (30H, m), 1.46 (2H, m), 1.98 (1H, m), 2.18–2.30 (3H, m), 2.38 (1H, m), 2.6–2.9 (3H, m), 3.18 (2H, m), 3.35 (2H, d, J=11.7 Hz), 3.78 (2H, m), 4.09 (2H, m), 4.16 (4H, m), 5.72 (1H, m), 5.75 (1H, m), 5.91 (1H, brt), 7.46 (3H, m), 7.64 (2H, m), 13.26 (1H, brs).

Example 9

{6-[(Tetradecylamino)carbonyl]-3-cyclohexenyl}methyl 4-methyltetrahydro-1(2H)-pyrazinecarboxylate (Compound 9)

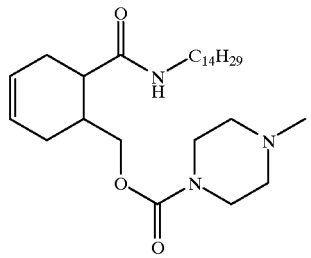

(1) 6-(Hydroxymethyl)-N-tetradecyl-3-cyclohexene-1-carboxamide

1-Tetradecylamine (3.51 g) was added to cis-4-cyclohexene-1,2-dicarboxylic anhydride (2.50 g) and stirred for 5 hours at 140° C. The reaction mixture was suspended into a mixed solution of 2-propanol (125 ml) and water (21 ml) and then sodium borohydride (3.11 g) was added thereto at room temperature. After being stirred for 67.5 hours at room temperature, the reaction mixture was acidified with dilute hydrochloric acid. The resulting solid was collected by filtration under a vacuum, washed with water, and dried, thereby yielding the entitled compound (5.38 g) as white solid.

$^1$H-NMR (CDCl$_3$) δ:0.88 (3H, t, J=6.8 Hz), 1.2–1.35 (22H, m), 1.48 (2H, m), 1.85 (1H, m), 2.09–2.43 (4H, m), 2.84 (1H, ddd, J=5.4, 5.4, 3.9 Hz), 3.19 (1H, m), 3.30 (1H, m), 3.54 (1H, brs), 3.62 (2H, m), 5.74 (1H, m), 5.78 (1H, m), 5.98 (1H, brt).

(2) {6-[(Tetradecylamino)carbonyl]-3-cyclohexenyl}methyl 4-methyltetrahydro-1(2H)-pyrazinecarboxylate Pyridine (0.83 ml) and phenyl chlorocarbonate (0.95 ml) were added to a solution of 6-(hydroxymethyl)-N-tetradecyl-3-cyclohexene-1-carboxamide (2.400 g) in chloroform (24 ml) while being cooled with ice. After being stirred for 2.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-Methylpiperazine (0.84 ml) was added to the residue and stirred for 2 hours at 70° C. The reaction mixture was purified by silica gel column chromatography (silica gel 100 g, ethyl acetate (260 ml) and then chloroform:methanol=40:1–30:1), thereby yielding the entitled compound (2.946 g) as white solid.

$^1$H-NMR (CDCl$_3$) δ:0.88 (3H, t, J=6.6 Hz), 1.2–1.35 (22H, m), 1.49 (2H, m), 2.05 (1H, m), 2.16–2.48 (4H, m), 2.30 (3H, s), 2.36 (4H, t, J=4.9 Hz), 2.66 (1H, ddd, J=6.8, 6.8, 3.4 Hz), 3.24 (2H, m), 3.48 (4H, t, J=4.9 Hz), 4.02 (1H, dd, J=10.7, 7.8 Hz), 4.19 (1H, dd, J=10.7, 5.9 Hz), 5.71 (1H, m), 5.75 (1H, m), 6.14 (1H, brt).

Example 10

{6-[(Tetradecylamino)carbonyl]-3-cyclohexenyl}methyl 4-methyltetrahydro-1(2H)-pyrazinecarboxylate hydrochloride (Compound 10)

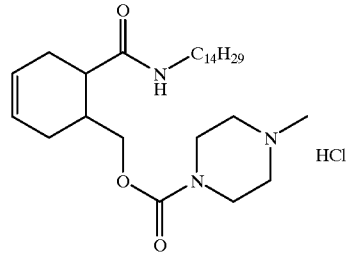

4N Hydrochloric acid/ethyl acetate solution (1.58 ml) was added to a solution of {6-[(tetradecylamino)carbonyl]-3-cyclohexenyl}methyl 4-methyltetrahydro-1(2H)-pyrazinecarboxylate (2.500 g) in ethyl acetate (25 ml). After being stirred for 30 minutes at room temperature, the reaction mixture was concentrated. The residue was recrystallized with ethyl acetate-ethanol mixed solution, thereby yielding the entitled compound (2.147 g) as white solid.

$^1$H-NMR (CDCl$_3$) δ: 0.88 (3H, t, J=6.8 Hz), 1.2–1.35 (22H, m), 1.47 (2H, m), 2.01 (1H, m), 2.22 (1H, m), 2.30 (2H, m), 2.41 (1H, m), 2.68 (1H, m), 2.81 (3H, s), 2.8–3.0 (2H, m), 3.23 (2H, m), 3.42 (2H, m), 3.71 (2H, m), 4.0–4.4 (4H, m), 5.76 (2H, m), 5.91 (1H, brt), 13.21 (1H, brs).

Example 11

[6-[[(2-Piperidinoethyl)amino]carbonyl]-3-cyclohexenyl]methyl N-octadecylcarbamate (Compound 11)

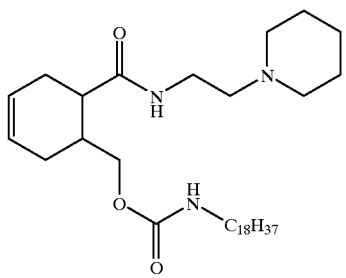

(1) 6-(Hydroxymethyl)-N-(2-piperidinoethyl)-3-cyclohexene-1-carboxamide

N-(2-Aminoethyl)piperidine (2.11 g) was added to cis-4-cyclohexene-1,2-dicarboxylic anhydride (2.50 g) and stirred for 6 hours at 140° C. The reaction mixture was suspended into a mixed solution of 2-propanol (125 ml) and water (21 ml) and then sodium borohydride (3.12 g) was added thereto at room temperature. After being stirred for 68 hours at room temperature, the reaction mixture was acidified with dilute hydrochloric acid and then concentrated. The residue was adjusted to pH 9 with saturated sodium hydrogencarbonate aqueous solution and 1N sodium hydroxide, and then extracted with ethyl acetate. The extract was washed with saturated brine, dried over sodium sulfate anhydride, and concentrated, thereby yielding a crude (3.34 g) containing the entitled compound as brown syrup.

$^1$H-NMR (CDCl$_3$) δ: 1.45 (2H, m), 1.58 (4H, m), 1.88 (1H, m), 2.1–2.5 (10H, m), 2.85 (1H, ddd, J=5.9, 5.9, 3.9 Hz), 3.34 (2H, m), 3.62 (2H, d, J=6.8 Hz), 5.73 (1H, m), 5.76 (1H, m), 6.71 (1H, brt).

(2) [6-[[(2-Piperidinoethyl)amino]carbonyl]-3-cyclohexenyl]methyl N-octadecylcarbamate Triethylamine (0.96 ml) and octadecyl isocyanate (2.2 ml) were added to a solution of 6-(hydroxymethyl)-N-(2-piperidinoethyl)-3-cyclohexene-1-carboxamide (1.65 g) in methylene chloride (22 ml). After being stirred for 15 hours at room temperature, triethylamine (0.96 ml) and octadecyl isocyanate (2.2 ml) were further added to the reaction mixture and stirred for 5 hours at room temperature. The insoluble matters were filtrated out under a vacuum and washed with chloroform. The filtrate and washings were combined together and the mixture was washed with saturated sodium hydrogencarbonate aqueous solution and saturated brine successively, dried over sodium sulfate anhydride, and concentrated. The residue was purified by silica gel column chromatography (silica gel 100 g, chloroform:methanol=30:1–10:1), thereby yielding the entitled compound (2.59 g) as white solid.

$^1$H-NMR (CDCl$_3$) δ: 0.88 (3H, t, J=6.8 Hz), 1.2–1.35 (30H, m), 1.45 (4H, m), 1.56 (4H, m), 2.04 (1H, m), 2.15–2.46 (10H, m), 2.70 (1H, ddd, J=6.4, 6.4, 3.4), 3.14 (2H, m), 3.33 (2H, m), 4.06 (2H, d, J=7.3 Hz), 4.75 (1H, brt), 5.72 (1H, m), 5.75 (1H, m), 6.56 (1H, brt).

Example 12

[6-[[(2-Piperidinoethyl)amino]carbonyl]-3-cyclohexenyl]methyl N-octadecylcarbamate hydrochloride (Compound 12)

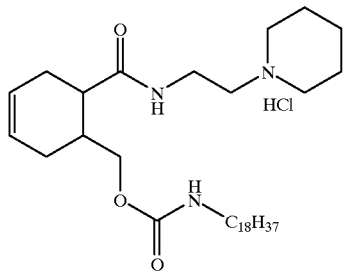

4N Hydrochloric acid/ethyl acetate solution (1.30 ml) was added to a solution of [6-[[(2-piperidinoethyl)amino]carbonyl]-3-cyclohexenyl]methyl N-octadecylcarbamate (2.431 g) in ethyl acetate (50 ml). After being stirred for 30 minutes at room temperature, the reaction mixture was concentrated. The residue was recrystallized with methanol-isopropyl ether mixed solution, thereby yielding the entitled compound (2.407 g) as white solid.

$^1$H-NMR (CDCl$_3$) δ: 0.88 (3H, t, J=6.8 Hz), 1.2–1.35 (30H, m), 1.50 (2H, m), 1.6–2.4 (11H, m), 2.66 (2H, m), 2.88 (1H, m), 3.13 (4H, m), 3.62 (3H, m), 3.78 (2H, m), 4.23 (1H, m), 5.67 (1H, m), 5.70 (1H, m), 5.77(1H, brt), 8.32 (1H, t, J=5.4 Hz), 11.23 (1H, brs).

Example 13

{6-[(Dodecylamino)carbonyl]-3,4-dimethyl-3-cyclohexenyl}methyl N-(2-piperidinoethyl) carbamate (Compound 13)

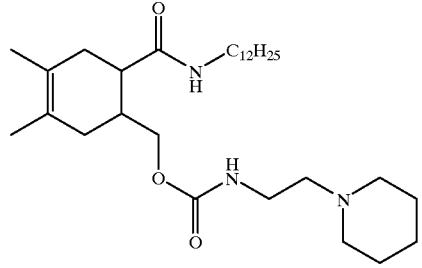

(1) N-Dodecyl-6-(hydroxymethyl)-3,4-dimethyl-3-cyclohexene-1-carboxamide

Dodecylamine (0.518 g) was added to 4,5-dimethyl-4-cyclohexene-1,2-dicarboxylic anhydride (0.500 g) and stirred for 4 hours at 140° C. The reaction mixture was dissolved into a mixed solution of 2-propanol (22 ml) and water (3.7 ml), and then sodium borohydride (0.529 g) was added thereto at room temperature. After being stirred for 68 hours at room temperature, the reaction mixture was acidified with 3N hydrochloric acid and then stirred with water added thereto. The deposited solid was collected by filtration under a vacuum, washed with water, and dried, thereby yielding the entitled compound (0.913 g) as white solid.

$^1$H-NMR (CDCl$_3$) δ: 0.88 (3H, t, J=6.8 Hz), 1.2–1.4 (18H, m), 1.45 (2H, m), 1.64 (3H, s), 1.67 (3H, s), 1.75 (1H, m), 2.01 (1H, m), 2.16 (1H, m), 2.23 (2H, m), 2.82 (1H, m), 3.15 (1H, m), 3.28 (1H, m), 3.55 (1H, dd, J=11.7, 9.3 Hz), 3.61 (1H, dd, J=11.7, 4.9 Hz), 5.91 (1H, brt).

(2) {6-[(Dodecylamino)carbonyl]-3,4-dimethyl-3-cyclohexenyl}methyl N-(2-piperidinoethyl) carbamate Pyridine (0.30 ml) and phenyl chlorocarbonate (0.34 ml) were added to a solution of N-dodecyl-6-(hydroxymethyl)-3,4-dimethyl-3-cyclohexene-1-carboxamide (0.855 g) in methylene chloride (9 ml) while being cooled with ice. After being stirred for 1.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-(2-Aminomethyl)piperidine (0.39 ml) was added to the residue and stirred for 2 hours at 70° C. The reaction mixture was purified by silica gel column chromatography (silica gel 50 g, chloroform:methanol=50:1–10:1), thereby yielding the entitled compound (0.975 g) as white solid.

$^1$H-NMR (CDCl$_3$) δ: 0.88 (3H, t, J=6.6 Hz), 1.2–1.4 (18H, m), 1.45 (4H, m), 1.57 (4H, m), 1.64 (3H, s), 1.65 (3H, s), 1.79 (1H, m), 1.92 (1H, m), 2.09 (1H, m), 2.14 (1H, m), 2.22 (1H, m), 2.37 (4H, m), 2.41 (2H, t, J=6.1 Hz), 2.65 (1H, m), 3.16–3.30 (4H, m), 3.95 (1H, dd, J=10.7, 7.8 Hz), 4.10 (1H, dd, J=10.7, 6.4 Hz), 5.27 (1H, brt), 6.10 (1H, brt).

Example 14

{6-[(Dodecylamino)carbonyl]-3,4-dimethyl-3-cyclohexenyl}methyl N-(2-piperidinoethyl) carbamate hydrochloride (Compound 14)

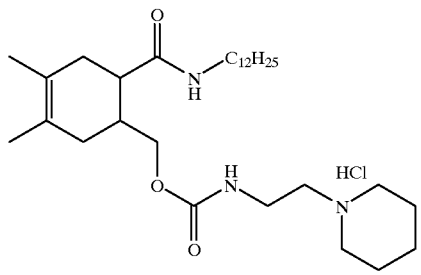

4N Hydrochloric acid/ethyl acetate solution (0.51 ml) was added to a solution of {6-[(dodecylamino)carbonyl]-3,4-dimethyl-3-cyclohexenyl}methyl N-(2-piperidinoethyl) carbamate (0.850 g) in ethyl acetate (9 ml) and then stirred for 30 minutes at room temperature. The reaction mixture was concentrated, thereby yielding the entitled compound (0.870 g) as white solid.

$^1$H-NMR (CDCl$_3$) δ: 0.88 (3H, t, J=6.8 Hz), 1.2–1.4 (18H, m), 1.48 (2H, m), 1.63 (3H, s), 1.64 (3H, s), 1.8–2.6 (1H, m), 2.7–2.85 (3H, m), 3.1–3.3 (4H, m), 3.55–3.75 (4H, m), 4.01 (2H, d, J=7.3 Hz), 6.42 (1H, brt), 7.01 (1H, brt), 11.27 (1H, brs).

Compounding Example 1
Hair Growth Tonic

| | |
|---|---|
| Compound 1 | 0.5 wt % |
| Pyridoxine dioctanoate | 0.1 |
| Pantothenyl ethyl ether | 0.2 |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |

<Preparation Method>

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

Compounding Example 2
Hair Regrowth Promoting Liquid Lotion

| | |
|---|---|
| Compound 3 | 0.2 wt % |
| Carpronium chloride | 1.0 |
| Pantothenyl ethyl ether | 0.5 |
| Diphenhydramine hydrochloride | 0.1 |
| Hinokitiol | 0.1 |
| dl-α-Tocopheryl acetate | 0.1 |
| Salicylic acid | 0.2 |
| 1-Menthol | 0.2 |
| Glycyrrhizinic acid | 0.1 |
| Sodium dl-pyrrolidonecarboxylate solution | 1.0 |
| Ethanol | 70.0 |
| Purified water | Balance |

<Preparation Method>

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

Compounding Example 3
Hair Tonic

| | |
|---|---|
| Compound 2 | 0.1 wt % |
| Paeony root extract (1,3-butylene glycol extract) | 0.01 |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

Compounding Example 4
Hair Tonic

| | |
|---|---|
| Paeonia extract (ethanol extract) | 5.0 wt% |
| Compound 5 | 0.05 |
| Compound 6 | 0.05 |
| Hinokitiol | 1.0 |
| Vitamin B$_6$ | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

Compounding Example 5
Hair Tonic

| | |
|---|---|
| Compound 4 | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |

| -continued | |
|---|---|
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-dimethyl-2-decyltetradecylamineoxide | 0.5 |
| Polyoxyethylene (40) hydrogenated castor oil | 0.5 |
| Succinic acid | Q.S. |
| Perfume and coloring agent | Q.S. |
| Purified water | Balance |

<Preparation Method>

A hair tonic was prepared according to Compounding Example 1.

Compounding Example 6

Hair Lotion

| | |
|---|---|
| 95% Ethanol | 90.0 wt % |
| Vitamin E acetate | 0.05 |
| Compound 7 | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |

<Preparation Method>

Polyoxyethylene (40) hydrogenated castor oil and perfume were dissolved in 95% ethanol. Then, purified water and the other ingredients were added and dissolved into the mixture successively with stirring to obtain a transparent liquid lotion.

Compounding Example 7

Hair Tonic

| | |
|---|---|
| Compound 8 | 0.1 wt % |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

Compounding Example 8

Hair Tonic

| | |
|---|---|
| Compound 9 | 0.5 wt % |
| Compound 10 | 0.1 |
| Hinokitiol | 1.0 |
| Vitamin B$_6$ | 0.2 |

| -continued | |
|---|---|
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10) monostearate | 2.0 |
| 70% Ethanol | Balance |

<Preparation Method>

Each of the above ingredients was added and dissolved into 70% ethanol successively with stirring to obtain a hair tonic.

Compounding Example 9

O/W Type Emulsion

| | |
|---|---|
| (Phase A) | |
| Polyoxyethylene (60) hydrogenated castor oil | 2.0 wt % |
| Glycerin | 10.0 |
| Dipropylene glycol | 10.0 |
| 1,3-Butylene glycol | 4.0 |
| Compound 11 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinylpolymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |

<Preparation Method>

Phases A and B were heated and dissolved, separately. Both were mixed and treated with a homomixer, thereby obtaining a gel. Phase D was gradually added to this gel and dispersed by the homomixer. Then, Phases C and E, which were mixed and dissolved in advance separately, were added to this gel dispersion successively. The mixture was emulsified by the homomixer to obtain an O/W type emulsion.

Compounding Example 10

Cream

| | |
|---|---|
| (Phase A) | |
| N,N-Dimethyl-2-tetradecylamineoxide | 2.5 wt % |
| Liquid paraffin | 5.0 |
| Cetostearyl alcohol | 5.5 |
| Glyceryl monostealate | 3.0 |
| Polyoxyethylene (20) 2-octyldodecyl ether | 3.0 |
| Propyl paraben | 0.3 |
| Perfume | 0.1 |
| (Phase B) | |
| Compound 12 | 1.0 |
| Glycerin | 8.0 |

| -continued | |
|---|---|
| Dipropylene glycol | 20.0 |
| Polyethylene glycol 4000 | 5.0 |
| Sodium hexametaphosphate | 0.005 |
| Ion-exchanged water | Balance |

<Preparation Method>
Phases A and B were heated and dissolved, separately. Both were mixed and emulsified by a homomixer to obtain a cream.

Compounding Example 11
Aerosol Spray

| (Stock solution) | |
|---|---|
| 95% Ethanol | 50.0 wt % |
| Glycyrrhizic acid | 0.1 |
| Compound 13 | 0.5 |
| Swertia herb extract | 0.1 |
| Sodium laurylsulfate | 0.1 |
| Polyoxyethylene (40) hydrogenated castor oil | 0.5 |
| Lactic acid | Q.S. |
| Sodium lactate | Q.S. |
| Perfume | Q.S. |
| Ion-exchanged water | Balance |
| (Filling formulation) | |
| Stock solution | 50.0 |
| Liquefied petroleum gas | 50.0 |

<Preparation Method>
A stock solution was prepared by mixing and dissolving the ingredients of stock solution. This stock solution was filled into a can and a valve was fit thereto. Liquefied petroleum gas was filled into the can to obtain an aerosol spray.

Compounding Example 12
Shampoo

| (1) Sodium cocoylmethyltaurate | 2.0 wt % |
|---|---|
| (2) Polyoxyethylene (8) oleyl ether | 2.0 |
| (3) Lauric acid diethanolamide | 4.0 |
| (4) Ethylene glycol fatty acid ester | 1.0 |
| (5) Glycerine | 0.2 |
| (6) Menthol | 0.1 |
| (7) Compound 14 | 0.1 |
| (8) Disodium edetate | 0.1 |
| (9) Perfume | Q.S. |
| (10) Purified water | Balance |

<Preparation Method>
The ingredient (10) was heated up to 70° C. The ingredients (1)–(9) were added to the heated ingredient (10) successively and the mixture was mixed and dissolved with stirring. The mixture was cooled to obtain a shampoo.

Compounding Example 13
Rinse

| (1) Stearyl trimethyl ammonium chloride | 1.5 wt % |
|---|---|
| (2) Dimethyl polysiloxane (20 cs) | 3.0 |
| (3) Polyoxyethylene (10) oleyl ether | 1.0 |

| -continued | |
|---|---|
| (4) Glycerin | 5.0 |
| (5) Compound 1 | 0.5 |
| (6) 4-tert-Butyl-4'-methoxydibenzoylmethane | Q.S. |
| (7) Ultraviolet absorber | Q.S. |
| (8) Purified water | Balance |

<Preparation Method>
The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

Compounding Example 14
Scalp Treatment

| (Stock solution) | |
|---|---|
| (1) Liquid paraffin | 27.0 wt % |
| (2) Stearic acid | 5.0 |
| (3) Cetanol | 5.0 |
| (4) Sorbitan monooleate | 2.0 |
| (5) Polyoxyethylene sorbitan monooleate | 3.0 |
| (6) Compound 5 | 0.1 |
| (7) 1,3-Butylene glycol | 5.0 |
| (8) Antiseptic | Q.S. |
| (9) Purified water | Balance |
| (Filling formulation) | |
| Stock solution | 50.0 |
| Liquefied petroleum gas | 50.0 |

<Preparation Method>
The ingredients (5) and (6) were dissolved into ingredients (1) to (4). After being dissolved with heating up to 80° C., the mixture was cooled down to 30° C. This mixture was added to the mixed solution of the ingredients (7) to (9), which was maintained at 30° C., and mixed with stirring to obtain a stock solution. This stock solution was filled into a can together with liquefied petroleum gas to obtain a scalp treatment.

Compounding Example 15
Scalp Treatment

| (Stock solution) | |
|---|---|
| (1) Hinokitiol | 0.1 wt % |
| (2) Swertia herb extract | 1.0 |
| (3) Vitamin $B_6$ | 0.1 |
| (4) Vitamin E | 0.01 |
| (5) Menthol | 0.1 |
| (6) Salicylic acid | 0.001 |
| (7) Compound 3 | 0.1 |
| (8) Polyoxyethylene sorbitan monooleate | 0.1 |
| (9) Propylene glycol | 2.0 |
| (10) 75% Ethanol | Balance |
| (Filling formulation) | |
| Stock solution | 50.0 |
| Dimethyl ether | 50.0 |

<Preparation Method>
A scalp treatment was prepared in the similar manner to Compounding Example 14.

In the following, the compounds and manufacturing processes thereof in accordance with the present invention are exemplified.

Compound 15

[6-[[N-(2-Dimethylamino)ethyl]carbamoyloxy]methyl]-3-cyclohexenyl]-N-octadecylformamide

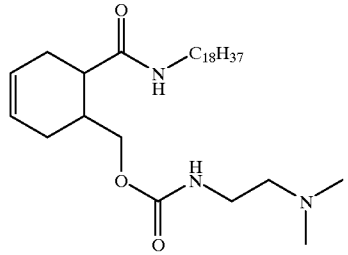

In Example 1, N,N-dimethylethylenediamine is used in the place of N,N-dimethyl-1,3-propanediamine to obtain the entitled compound.

Compound 16

[6-[[N-(Dimethylamino)carbamoyloxy]methyl]-3-cyclohexenyl]-N-octadecylformamide

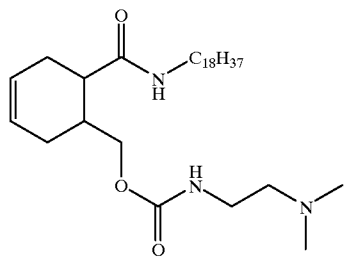

In Example 1, 1,1-dimethylhydrazine is used in the place of N,N-dimethyl-1,3-propanediamine to obtain the entitled compound.

Compound 17

[6-[[N-[3-(1-Imidazolyl)propyl]carbamoyloxy]methyl]-3-cyclohexenyl]-N-octadecylformamide

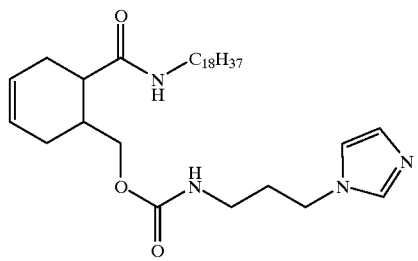

In Example 1, 1-(3-aminopropyl)imidazole is used in the place of N,N-dimethyl-1,3-propanediamine to obtain the entitled compound.

Compound 18

[6-[[N-(2-Piperazinylethyl)carbamoyloxy]methyl]-3-cyclohexenyl]-N-octadecylformamide

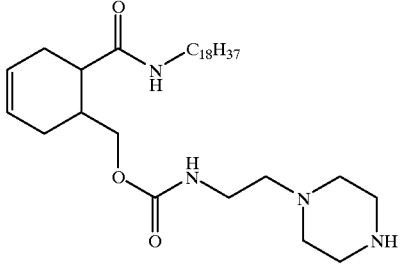

In Example 1, 1-(2-aminoethyl)piperazine is used in the place of N,N-dimethyl-1,3-propanediamine to obtain the entitled compound.

Compound 19

[6-[[N-(2-Aminoethyl)carbamoyloxy]methyl]-3-cyclohexenyl]-N-octadecylformamide

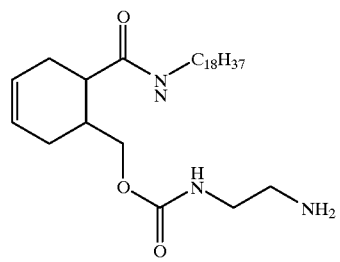

In Example 1, ethylenediamine is used in the place of N,N-dimethyl-1,3-propanediamine to obtain the entitled compound.

Compound 20

[6-[[N-(2-Diethylamino)ethyl]carbamoyloxy]methyl]-3-cyclohexenyl]-N-octadecylformamide

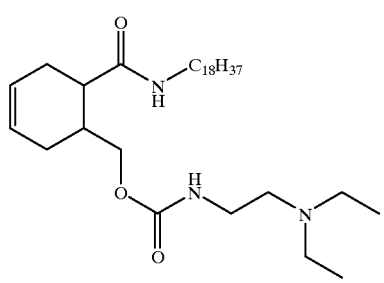

In Example 1, N,N-diethylethylenediamine is used in the place of N,N-dimethyl-1,3-propanediamine to obtain the entitled compound.

Compound 21

[6-[[N-[3-[Bis(2-hydroxyethyl)amino]propyl]
carbamoyloxy]methyl]-3-cyclohexenyl]-N-
octadecylformamide

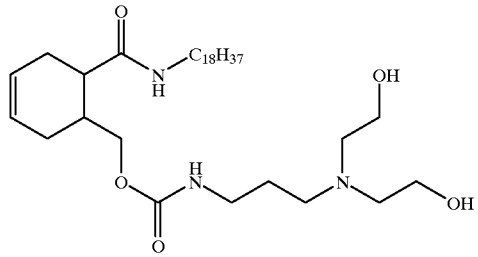

In Example 1, N-(3-aminopropyl)diethanolamine is used in the place of N,N-dimethyl-1,3-propanediamine to obtain the entitled compound.

Compound 22

[6-[[N-[3-(N-Methyl-N-phenylamino)propyl]
carbamoyloxy]methyl]-3-cyclohexenyl]-N-
octadecylformamide

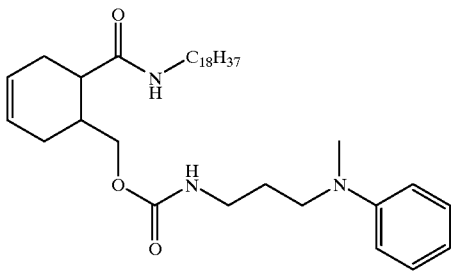

In Example 1, N-(3-aminopropyl)-N-methylaniline is used in the place of N,N-dimethyl-1,3-propanediamine to obtain the entitled compound.

Compound 23

[6-[[N-(3-Dibenzylamino)propyl]carbamoyloxy]
methyl]-3-cyclohexenyl]-N-octadecylformamide

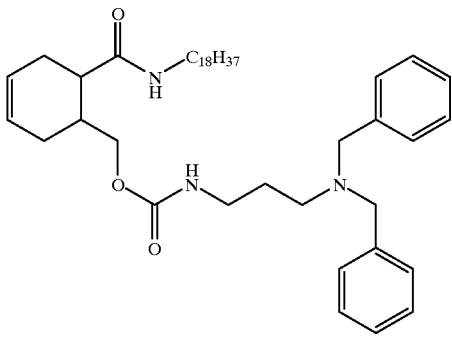

In Example 1, N,N-dibenzyl-1,3-propanediamine is used in the place of N,N-dimethyl-1,3-propanediamine to obtain the entitled compound.

Compound 24

[4-Chloro-6-[[N-[3-(dimethylamino)propyl]
carbamoyloxy]methyl]-3-cyclohexenyl]-N-
octadecylformamide

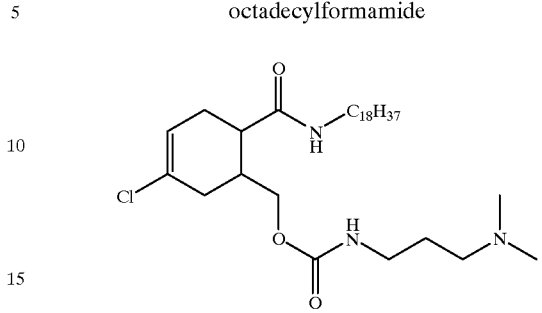

In Example 1, 5-chloro-4,7,3a,7a-tetrahydroisobenzofuran-1,3-dione is used in the place of 4,7,3a,7a-tetrahydroisobenzofuran-1,3-dione to obtain the entitled compound.

Compound 25

[6-[[N-[3-(Dimethylamino)propyl]carbamoyloxy]
methyl]-4-methyl-3-cyclohexenyl]-N-
octadecylformamide

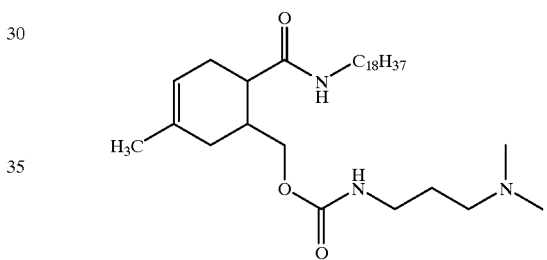

In Example 1, 5-methyl-4,7,3a,7a-tetrahydroisobenzofuran-1,3-dione is used in the place of 4,7,3a,7a-tetrahydroisobenzofuran-1,3-dione to obtain the entitled compound.

Compound 26

[5-Acetyl-6-[[N-[3-(dimethylamino)propyl]
carbamoyloxy]methyl]-3-cyclohexenyl]-N-
octadecylformamide

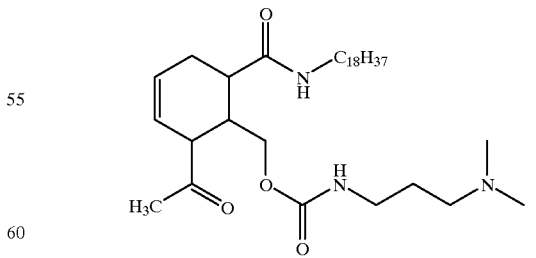

In Example 1, 4-acetyl-4,7,3a,7a-tetrahydroisobenzofuran-1,3-dione is used in the place of 4,7,3a,7a-tetrahydroisobenzofuran-1,3-dione to obtain the entitled compound.

Compound 27

[6-[[N-[3-(Dimethylamino)propyl]carbamoyloxy]
methyl]-2-nitro-3-cyclohexenyl]-N-
octadecylformamide

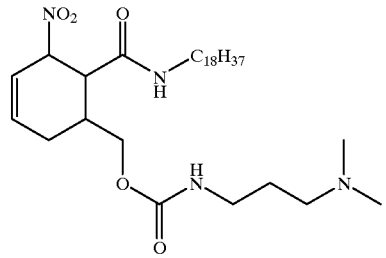

In Example 1, 4-nitro-4,7,3a,7a-tetrahydroisobenzofuran-1,3-dione is used in the place of 4,7,3a,7a-tetrahydroisobenzofuran-1,3-dione to obtain the entitled compound.

Compound 28

[2-Cyano-6-[[N-[3-(dimethylamino)propyl]
carbamoyloxy]methyl]-3-cyclohexenyl]-N-
octadecylformamide

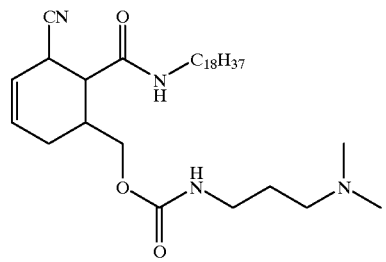

In Example 1, 4-cyano-4,7,3a,7a-tetrahydroisobenzofuran-1,3-dione is used in the place of 4,7,3a,7a-tetrahydroisobenzofuran-1,3-dione to obtain the entitled compound.

Compound 29

[6-[[N-[3-(dimethylamino)propyl]carbamoyloxy]
methyl]-5-methoxycarbonyl-3-cyclohexenyl]-N-
octadecylformamide

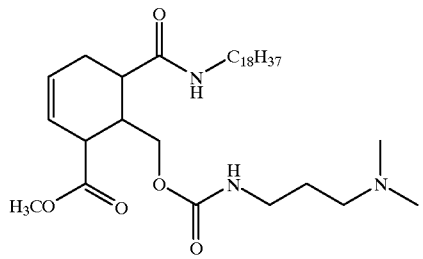

In Example 1, 4-methoxycarbonyl-4,7,3a,7a-tetrahydroisobenzofuran-1,3-dione is used in the place of 4,7,3a,7a-tetrahydroisobenzofuran-1,3-dione to obtain the entitled compound.

Compound 30

[5-Carbamoyl-6-[[N-[3-(dimethylamino)propyl]
carbamoyloxy]methyl]-3-cyclohexenyl]-N-
octadecylformamide

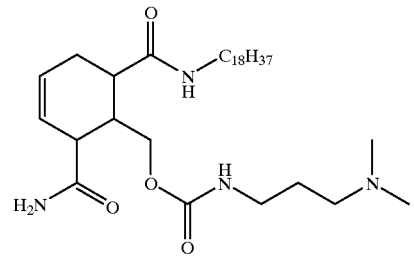

In Example 1, 4-carbamoyl-4,7,3a,7a-tetrahydroisobenzofuran-1,3-dione is used in the place of 4,7,3a,7a-tetrahydroisobenzofuran-1,3-dione to obtain the entitled compound.

Compound 31

[6-[[N-[3-(Dimethylamino)propyl]carbamoyloxy]
methyl]-5-(N-methylcarbamoyl)-3-cyclohexenyl]-N-
octadecylformamide

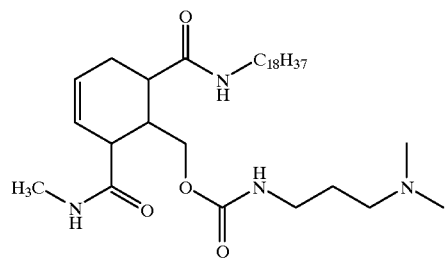

In Example 1, 4-(N-methylcarbamoyl)-4,7,3a,7a-tetrahydroisobenzofuran-1,3-dione is used in the place of 4,7,3a,7a-tetrahydroisobenzofuran-1,3-dione to obtain the entitled compound.

Compound 32

[3-(Dimethylamino)-6-[[N-[3-(dimethylamino)
propyl]carbamoyloxy]methyl]-3-cyclohexenyl]-N-
octadecylformamide

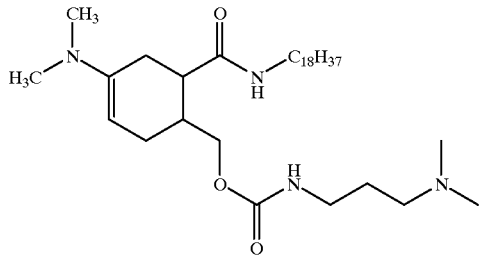

In Example 1, 5-(dimethylamino)-4,7,3a,7a-tetrahydroisobenzofuran-1,3-dione is used in the place of 4,7,3a,7a-tetrahydroisobenzofuran-1,3-dione to obtain the entitled compound.

Compound 33

[3-(Benzoylamino)-6-[[N-[3-(dimethylamino)propyl]carbamoyloxy]methyl]-3-cyclohexenyl]-N-octadecylformamide

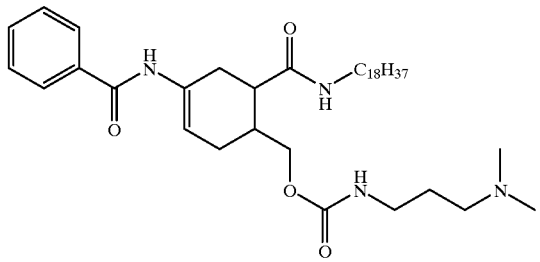

In Example 1, 5-(benzoylamino)-4,7,3a,7a-tetrahydroisobenzofuran-1,3-dione is used in the place of 4,7,3a,7a-tetrahydroisobenzofuran-1,3-dione to obtain the entitled compound.

Compound 34

[6-[[N-[3-(dimethylamino)propyl]carbamoyloxy]methyl]-3-methoxy-3-cyclohexenyl]-N-octadecylformamide

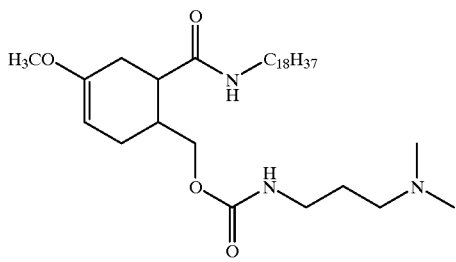

In Example 1, 5-methoxy-4,7,3a,7a-tetrahydroisobenzofuran-1,3-dione is used in the place of 4,7,3a,7a-tetrahydroisobenzofuran-1,3-dione to obtain the entitled compound.

Compound 35

[5-Acetoxy-6-[[N-[3-(dimethylamino)propyl]carbamoyloxy]methyl]-3-cyclohexenyl]-N-octadecylformamide

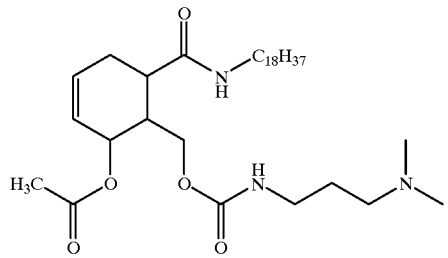

In Example 1, 4-acetoxy-4,7,3a,7a-tetrahydroisobenzofuran-1,3-dione is used in the place of 4,7,3a,7a-tetrahydroisobenzofuran-1,3-dione to obtain the entitled compound.

Compound 36

[6-[[N-[3-(Dimethylamino)propyl]carbamoyloxy]methyl]-3-cyclohexenyl]-N-methyl-N-octadecylformamide

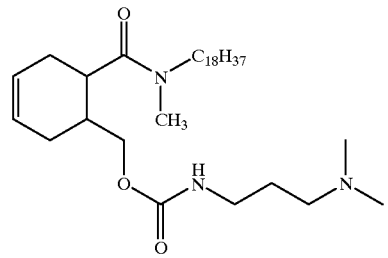

[6-(Hydroxymethyl)-3-cyclohexenyl]-N-octadecylformamide obtained in Example 1 (2) is reacted with trityl bromide in acetone in the presence of potassium carbonate to obtain N-octadecyl-[6-(trityloxymethyl)-3-cyclohexenyl]formamide.

This compound is reacted with methyl bromide in acetone in the presence of potassium carbonate to obtain N-methyl-N-octadecyl-[6-(trityloxymethyl)-3-cyclohexenyl]formamide.

This compound is reacted in ethanol under the reflux temperature in the presence of p-toluenesulfonyl chloride to obtain [6-(hydroxymethyl)-3-cyclohexenyl]-N-methyl-N-octadecylformamide.

In Example 1 (3), this compound is used in the place of [6-(hydroxymethyl)-3-cyclohexenyl]-N-octadecylformamide to obtain the entitled compound.

Compound 37

N-Acetyl-[6-[[N-acetyl-N-[3-(dimethylamino)propyl]carbamoyloxy]methyl]-3-cyclohexenyl]-N-octadecylformamide

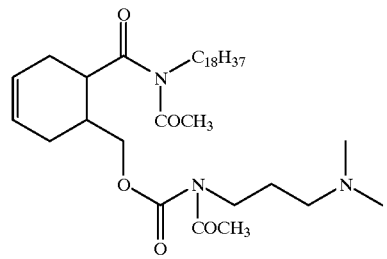

[6-[[N-[3-(Dimethylamino)propyl]carbamoyloxy]methyl]-3-cyclohexenyl]-N-octadecylformamide obtained in Example 1 is acetylated to obtain the entitled compound.

Compound 38

[6-[[[N-[3-(Dimethylamino)propyl]-N-(methylcarbamoyl)]carbamoyloxy]methyl]-3-cyclohexenyl]-N-(methylcarbamoyl)-N-octadecylformamide

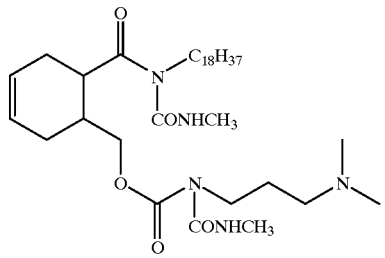

[6-[[N-[3-(Dimethylamino)propyl]carbamoyloxy]methyl]-3-cyclohexenyl]-N-octadecylformamide obtained in Example 1 is methylcarbamoylated to obtain the entitled compound.

Compound 39

[6-[[4-(Dimethylamino)butoxy]methyl]-3-cyclohexenyl]-N-methyl-N-octadecylformamide

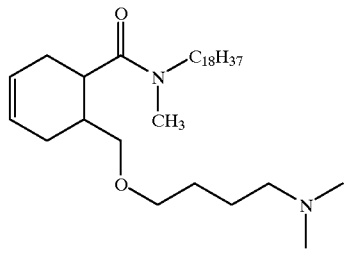

[6-(Hydroxymethyl)-3-cyclohexenyl]-N-methyl-N-octadecylformamide obtained in Compound 36 is reacted with 1-bromo-4-chlorobutane in acetone in the presence of potassium carbonate at the reflux temperature to obtain [6-(4-chlorobutoxymethyl)-3-cyclohexenyl]-N-methyl-N-octadecylformamide.

This compound and dimethylamine are reacted in acetone in the presence of potassium carbonate at the reflux temperature to obtain the entitled compound.

Compound 40

N-Methyl-[6-[[4-(morpholino)butoxy]methyl]-3-cyclohexenyl]-N-octadecylformamide

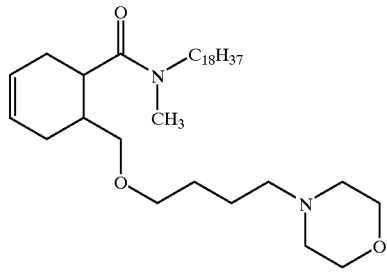

[6-(Hydroxymethyl)-3-cyclohexenyl]-N-methyl-N-octadecylformamide obtained in Compound 36 is reacted with 1-bromo-4-chlorobutane in acetone in the presence of potassium carbonate at the reflux temperature to obtain [6-(4-chlorobutoxymethyl)-3-cyclohexenyl]-N-methyl-N-octadecylformamide.

This compound and morpholine are reacted in acetone in the presence of potassium carbonate at the reflux temperature to obtain the entitled compound.

Compound 41

[6-(N-Octadecylcarbamoyl)-3-cyclohexenyl]methyl 4-(dimethylamino)butylate

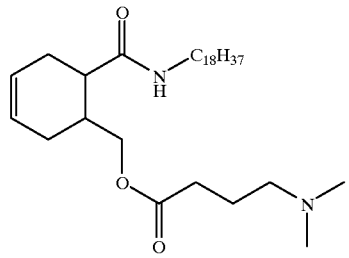

DCC is added to a solution of [6-(hydroxymethyl)-3-cyclohexenyl]-N-octadecylformamide and 4-(N,N-dimethylamino)butylic acid in N,N-dimethylformamide and then the reaction is effected at room temperature to obtain the entitled compound.

Compound 42

[6-[[3-(dimethylamino)propylamino]methyl]-3-cyclohexenyl]-N-methyl-N-octadecylformamide

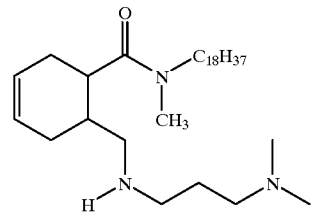

A solution of [6-(hydroxymethyl)-3-cyclohexenyl]-N-methyl-N-octadecylformamide obtained in Compound 36 and p-toluenesulfonyl chloride in 1,4-dioxane is added to sodium hydroxide solution and the reaction is effected at room temperature to obtain N-methyl-N-octadecyl-[6-(tosyloxymethyl)-3-cyclohexenyl]formamide.

This compound and N,N-dimethyl-1,3-propanediamine are reacted in acetone in the presence of potassium carbonate at the reflux temperature to obtain the entitled compound.

Compound 43

N-Methyl-[6-[[(3-morpholinopropyl)amino]methyl]-3-cyclohexenyl]-N-octadecyl formamide

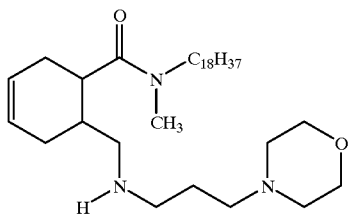

A solution of [6-(hydroxymethyl)-3-cyclohexenyl]-N-methyl-N-octadecylformamide obtained in Compound 36 and p-toluenesulfonyl chloride in 1,4-dioxane is added to sodium hydroxide solution and the reaction is effected at room temperature to obtain N-methyl-N-octadecyl-[6-(tosyloxymethyl)-3-cyclohexenyl]formamide.

This compound and 1-(3-aminopropyl)morpholine are reacted in acetone in the presence of potassium carbonate at the reflux temperature to obtain the entitled compound.

Compound 44

N-[3-(Dimethylamino)propyl]-{6-[(N-octadecylcarbamoyloxy)methyl]-3-cyclohexenyl}formamide

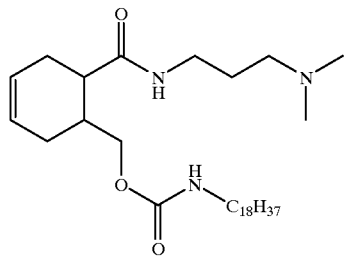

In Example 11 (1), N,N-dimethyl-1,3-propanediamine is used in the place of N-(2-aminoethyl)piperidine to obtain N-[3-(dimethylamino)propyl]-6-(hydroxymethyl)-3-cyclohexene-1-carboxamide.

In Example 11 (2), this compound is used in the place of 6-(hydroxymethyl)-N-(2-piperidinoethyl)-3-cyclohexene-1-carboxamide to obtain the entitled compound.

Compound 45

N-[3-(Dimethylamino)propyl]-N-methyl-[6-(octadecyloxymethyl)-3-cyclohexenyl]formamide

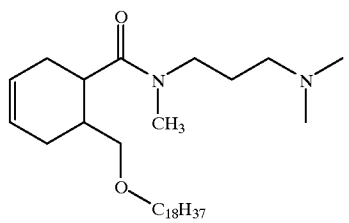

In Example 1 (1), 1-amino-3-chloropropane is used in the place of octadecylamine to obtain 2-(3-chloropropyl)-4,7,3a,7a-tetrahydroisoindole-1,3-dione.

In the similar manner to Example 1 (2), this compound is subjected to the reaction with sodium borohydride to obtain N-(3-chloropropyl)-[6-(hydroxymethyl)-3-cyclohexenyl]formamide.

This compound is reacted with 1-bromooctadecane in acetone in the presence of potassium carbonate at the reflux temperature to obtain N-(3-chloropropyl)-[6-(octadecyloxymethyl)-3-cyclohexenyl]formamide.

This compound is reacted with bromomethane in acetone in the presence of potassium carbonate at the reflux temperature to obtain N-(3-chloropropyl)-N-methyl-[6-(octadecyloxymethyl)-3-cyclohexenyl]formamide.

This compound and dimethylamine are reacted in acetone in the presence of potassium carbonate at the reflux temperature to obtain the entitled compound.

Compound 46

[6-[N-[3-(Dimethylamino)propyl]carbamoyl]-3-cyclohexenyl]methyl octadecanoate

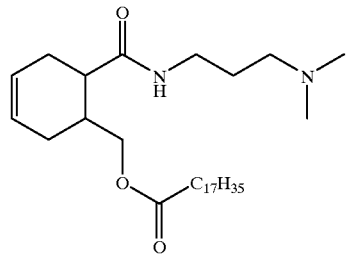

DCC is added to a solution of N-[3-(dimethylamino)propyl]-[6-(hydroxymethyl)-3-cyclohexenyl]formamide and stearic acid in N,N-dimethylformamide and then the reaction is effected at room temperature to obtain the aimed compound.

Compound 47

N-[3-(Dimethylamino)propyl]-N-methyl-[6-(octadecylaminomethyl)-3-cyclohexenyl]formamide

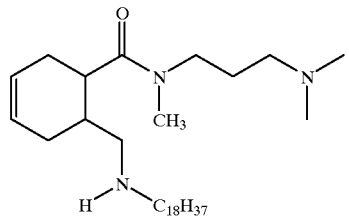

N-(3-Chloropropyl)-[6-(hydroxymethyl)-3-cyclohexenyl]formamide obtained in Compound 45 and bromomethane are reacted in acetone in the presence of potassium carbonate at the reflux temperature to obtain N-(3-chloropropyl)-[6-(hydroxymethyl)-3-cyclohexenyl]-N-methylformamide.

A solution of this compound and p-toluenesulfonyl chloride in 1,4-dioxane is added to sodium hydroxide solution and the reaction is effected at room temperature to obtain N-(3-chloropropyl)-N-methyl-[6-(tosyloxymethyl)-3-cyclohexenyl]formamide.

This compound and octadecylamine are reacted in acetone in the presence of potassium carbonate at the reflux temperature to obtain N-(3-chloropropyl)-N-methyl-[6-(octadecylaminomethyl)-3-cyclohexenyl]formamide.

This compound and dimethylamine are reacted in acetone in the presence of potassium carbonate at the reflux temperature to obtain the entitled compound.

Compound 48

N-Methyl-[6-(octadecylaminomethyl)-3-cyclohexenyl]-N-[3-(piperidino)propyl]formamide

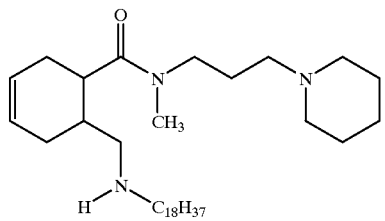

N-(3-Chloropropyl)-N-methyl-[6-(octadecylaminomethyl)-3-cyclohexenyl]formamide obtained in Compound 47 and piperidine are reacted in acetone in the presence of potassium carbonate at the reflux temperature to obtain the entitled compound.

Compound 49

{6-[(4-Methylpiperazinyl)carbonyl]-3-cyclohexenyl}methyl N-octadecylcarbamate

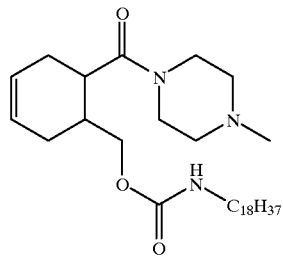

4,7,3a,7a-Tetrahydroisobenzofuran-1,3-dione is added to a solution sodium borohydride in 2-propanol at room temperature and reacted to obtain 4,7,3a,7a-tetrahydroisobenzofuran-1(3H)-one.

This compound and N-methylpiperazine are reacted without a solvent at 70° C. to obtain 6-(hydroxymethyl)-3-cyclohexenyl 4-methylpiperazinyl ketone.

In Example 11 (2), this compound is used in the place of 6-(hydroxymethyl)-N-(2-piperidinoethyl)-3-cyclohexene-1-carboxamide to obtain the entitled compound.

What is claimed is:

1. A [6-(substituted-methyl)-3-cyclohexenyl]formamide compound or a salt thereof expressed by the following formula (I):

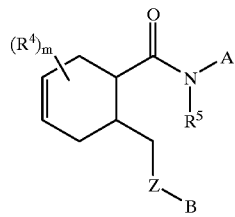

(I)

wherein each of A and B is $R^1$ or —$(CH_2)n$-$NR^2R^3$, wherein when A is $R^1$, B is —$(CH_2)n$-$NR^2R^3$ and when A is —$(CH_2)n$-$NR^2R^3$, B is $R^1$;

Z is —O—, —OCO—, —OCONR$^6$— or —NR$^6$—;

$R^1$ is a hydrocarbon group having 10 to 30 carbon atoms;

$R^2$ and $R^3$ individually represent a hydrogen atom, a lower alkyl group, a phenyl group or a benzyl group, or together represent a heterocycle having 3–7 members;

when A is —$(CH_2)n$-$NR^2R^3$, —$NR^5$—A may be Group W, and when —Z—B is —OCONR$^6$—$(CH_2)n$-$NR^2R^3$ or —NR$^6$—$(CH_2)n$-$NR^2R^3$, —Z—B may be a group of —OCO—W or Group W, wherein said Group W is expressed by the following Formula:

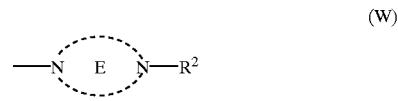

(W)

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group, and when A is —$(CH_2)n$-$NR^2R^3$, —$NR^5$—A may be said Group W;

$R^6$ is a hydrogen atom, a lower alkyl group, a lower acyl group or a lower alkylcarbamoyl group, and when —Z—B is —OCONR$^6$—$(CH_2)n$-$NR^2R^3$ or —NR$^6$—$(CH_2)n$-$NR^2R^3$, —Z—B may be —OCO—W or said Group W;

m is an integer of 0–2; and n is an integer of 0–5.

2. A [6-(substituted-methyl)-3-cyclohexenyl]formamide compound or a salt thereof according to claim 1, wherein A is $R^1$ and B is —$(CH_2)n$-$NR^2R^3$.

3. A [6-(substituted-methyl)-3-cyclohexenyl]formamide compound or a salt thereof according to claim 1, wherein A is —$(CH_2)n$-$NR^2R^3$ and B is $R^1$.

4. A [6-(substituted-methyl)-3-cyclohexenyl]formamide compound or a salt thereof according to claim 1, wherein Z is —OCONR$^6$—.

5. A [6-(substituted-methyl)-3-cyclohexenyl]formamide compound or a salt thereof according to claim 4, wherein $R^6$ is a hydrogen atom.

6. A [6-(substituted-methyl)-3-cyclohexenyl]formamide compound or a salt thereof according to claim 4, which is expressed by the following formula (IA):

(IA)

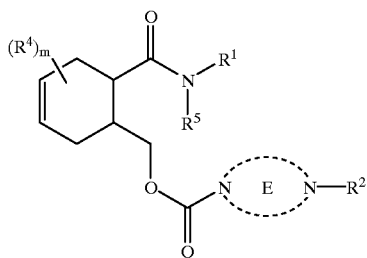

wherein ring E is a heterocycle of 6 or 7 members including two nitrogen atoms;

$R^1$ is a hydrocarbon group having 10 to 30 carbon atoms;

$R^2$ is a hydrogen atom, a lower alkyl group, a phenyl group or a benzyl group;

$R^4$ is selected from the group consisting of a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; and m is an integer of 0–2.

7. A [6-(substituted-methyl)-3-cyclohexenyl]formamide compound or a salt thereof according to claim 1, wherein Z is —$NR^6$—.

8. A [6-(substituted-methyl)-3-cyclohexenyl]formamide compound or a salt thereof according to claim 7, wherein $R^6$ is a hydrogen atom.

9. A [6-(substituted-methyl)-3-cyclohexenyl]formamide compound or a salt thereof according to claim 1, wherein Z is —O—.

10. A [6-(substituted-methyl)-3-cyclohexenyl]formamide compound or a salt thereof according to claim 1, wherein $R^1$ is an alkyl group having 10 to 30 carbon atoms.

11. A [6-(substituted-methyl)-3-cyclohexenyl]formamide compound or a salt thereof according to claim 1, wherein m is 0.

12. A [6-(substituted-methyl)-3-cyclohexenyl]formamide compound or a salt thereof according to claim 1, wherein $R^5$ is a hydrogen atom.

13. A [6-(substituted-methyl)-3-cyclohexenyl]formamide compound or a salt thereof according to claim 1, wherein n is an integer of 2–5.

14. A hair growth promoting composition comprising an affective amount of the [6-(substituted-methyl)-3-cyclohexenyl]formamide compound or the pharmacologically acceptable salt thereof according to claim 1.

15. An External preparation for skin comprising the [6-(substituted-methyl)-3-cyclohexenyl]formamide compound or the pharmacologically acceptable salt thereof according to claim 1.

16. A method for promoting hair growth which comprises applying an effective amount of the [6-(substituted-methyl)-3-cyclohexenyl]formamide compound or the pharmacologically acceptable salt thereof according to claim 1 on skin of mammals.

17. A method for promoting hair growth according to claim 16, wherein the skin of mammals is human scalp.

* * * * *